United States Patent [19]
Yamaoka et al.

[11] Patent Number: 5,804,410
[45] Date of Patent: Sep. 8, 1998

[54] NUCLEIC ACID SEQUENCE ENCODING TRYPSIN-LIKE ENZYME AND PROCESS FOR PRODUCING THE ENZYME

[75] Inventors: Kazuyoshi Yamaoka; Hiroko Ogawa; Yoshinori Sugimoto; Kenichi Masuda; Tetsuya Suga; Kenichiro Takagi, all of Hino; Susumu Yasuoka, Tokushima, all of Japan

[73] Assignee: Teijin Limited, Osaka, Japan

[21] Appl. No.: 508,448

[22] Filed: Jul. 28, 1995

[30] Foreign Application Priority Data

Jul. 29, 1994 [JP] Japan ................................ 6-178607

[51] Int. Cl.$^6$ .......................... C12P 21/06; C07H 17/00; C12N 9/00
[52] U.S. Cl. ................. 435/69.1; 435/183; 435/252.3; 435/320.1; 435/325; 435/213; 536/23.2
[58] Field of Search .......................... 435/213, 320.1, 435/325, 69.1, 183, 252.3; 536/23.2

[56] References Cited

U.S. PATENT DOCUMENTS

| | | | |
|---|---|---|---|
| 4,745,051 | 5/1988 | Smith et al. | 435/68 |
| 4,879,236 | 11/1989 | Smith et al. | 435/235 |
| 5,017,489 | 5/1991 | Pasternack et al. | 435/196 |

FOREIGN PATENT DOCUMENTS

| | | |
|---|---|---|
| 60057 | 9/1982 | European Pat. Off. . |
| 0 363 127 | 4/1990 | European Pat. Off. . |
| 57-159489 | 10/1982 | Japan . |
| 60-37988 | 2/1985 | Japan . |
| 2-171198 | 7/1990 | Japan . |
| 94/25583 | 11/1994 | WIPO . |

OTHER PUBLICATIONS

Smith et al., "Journal of Biological Chemistry", vol. 259, No. 17, pp. 11046–11051, Sep. 10, 1984.
The Japanese Journal of Thoracic Diseases, vol. 30, Supplement, Apr./1992, p. 280, G–77, p. 319, I–36 and its English translation.
The Japanese Journal of Thoracic Diseases, vol. 31, Supplement, Mar./1993, p. 311, K1–58 and its English translation.
The Society of Japanese Virologist, the 42nd General Meeting Lecture Extracts, p. 201, No. 4022 and its English translation.
Leytus et al., "A Novel Trypsin–like Serine Protease (Hepsin) with a Putative Transmembrane Domain Expressed by Human Liver and Hepatoma Cells", Biochemistry, vol. 27, pp. 1067–1074, 1988.
Tanaka et al., "Mammalian Tissue Trypsin–like Enzymes", The Journal of Biological Chemistry, vol. 258, No. 22, pp. 13552–13556, Nov. 25, 1993.
72nd Annual Meeting of the American Society of Biological Chemist, St. Louis Mo., USA, May 31–Jun. 4, 1981, Federal Proceedings 40 (6), 1981, 1717, Coden; Fepra7 Issn: 0014–9446, Johnson D A A "Trypsin–like neutral Proteinase From Human Lung Tissue".
Orlowski et al., "Lung Lymph Capillary Injury–related Protease", American Journal of Physiology:Lung Cellular and Molecular Physiology, vol. 1, No. 2, pp. 202–208, Oct. 1989.
Yu et al., "Prostasin is A Novel Human Serine Proteinase from Seminal Fluid", The Journal of Biological Chemistry, vol. 269, No. 29, pp. 18843–18848, Jul. 22, 1994.
Patent Abstracts of Japan, vol. 950, No. 003 & JP–A–07 067640 (Teijin Ltd) Mar. 14, 1995.
Girard et al., "Ultrasonic Method of Sputum Homogenization and its Application in the Study of the Enzymic Content of Sputum", Clinica Chimica Acta, vol. 113, No. 1, pp. 105–109, Jun. 2, 1981.

*Primary Examiner*—Karen Carlson
*Attorney, Agent, or Firm*—Wenderoth, Lind & Ponack, L.L.P.

[57] ABSTRACT

This invention provides a nucleic acid sequence encoding a trypsin-like enzyme which can be present at the trachea of human lungs, and can selectively digest a synthetic substrate for trypsin and a synthetic substrate for thrombin, and fibrinogen; and a process for producing the trypsin-like enzyme by genetic engineering utilizing the nucleic acid sequence.

9 Claims, 6 Drawing Sheets

Lane 1: Molecular-weight marker
Lane 2: Trypsin-like enzyme

Influence of trypsin-like enzyme on thrombin-induced coagulation time of fibrinogen Lane 1: Trypsin-like enzyme
Lane 2: Molecular-weight marker

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single (D) TOPOLOGY: linear (ii) MOLECULE TYPE: peptide (v) FRAGMENT TYPE: N-terminus fragment (vi) ORIGINAL SOURCE:
    (A) ORGANISM: Homo sapiens (xi) SEQUENCE DESCRIPTION: SEQ ID NO:1:

```
Ile Leu Gly Gly Thr Glu Ala Glu Glu Gly Ser Trp Pro Trp Gln Val
 1               5                  10                 15
Ser Leu Arg Leu
            20
```

(2) INFORMATION FOR SEQ ID NO:2:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (A) NAME/KEY:
        (B) LOCATION:
        (C) IDENTIFICATION METHOD:
        (D) OTHER INFORMATION: /note= "N = C or I"

(xi) SEQUENCE DESCRIPTION: SEQ ID NO:2:

ATCYTNGGRG GNACNGAGGC          20

(2) INFORMATION FOR SEQ ID NO:3:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:3:

ARKCKMAGGC TSACYTG          17

(2) INFORMATION FOR SEQ ID NO:4:

(i) SEQUENCE CHARACTERISTICS:
        (A) LENGTH: 59 bases
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Homo sapiens
        (F) TISSUE TYPE: trachea (xi) SEQUENCE DESCRIPTION: SEQ ID NO:4:

ATCTTGGGGG GCACGGAGGC TGAGGAGGGA AGCTGGCCGT GGCAAGTCAG CCTGCGATT    59

(2) INFORMATION FOR SEQ ID NO:5:

(i) SEQUENCE CHARACTERISTICS:
        (A) LENGTH: 23 bases
        (B) TYPE: nucleic acid
        (C) STRANDEDNESS: single
        (D) TOPOLOGY: linear (  i  i  ) MOLECULE TYPE: other nucleic acid (synthetic DNA)

(  x  i  ) SEQUENCE DESCRIPTION: SEQ ID NO:5:

| ATCTTGGGGG GCACGGAGGC TGA | 23 |
|---|---|

( 2 ) INFORMATION FOR SEQ ID NO:6:

(  i  ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear (  i  i  ) MOLECULE TYPE: other nucleic acid (synthetic DNA)

(  x  i  ) SEQUENCE DESCRIPTION: SEQ ID NO:6:

| GAGGCTGAGG AGGGAAGCTG GCCGT | 25 |
|---|---|

( 2 ) INFORMATION FOR SEQ ID NO:7:

(  i  ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear (  i  i  ) MOLECULE TYPE: other nucleic acid (synthetic DNA)

(  x  i  ) SEQUENCE DESCRIPTION: SEQ ID NO:7:

| GACTCGAGTC GACATCGATT TTTTTTTTT TTTTT | 35 |
|---|---|

( 2 ) INFORMATION FOR SEQ ID NO:8:

(  i  ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear (  i  i  ) MOLECULE TYPE: other nucleic acid (synthetic DNA)

(  x  i  ) SEQUENCE DESCRIPTION: SEQ ID NO:8:

| GACTCGAGTC GACATCGAT | 19 |
|---|---|

( 2 ) INFORMATION FOR SEQ ID NO:9:

(  i  ) SEQUENCE CHARACTERISTICS:
        ( A ) LENGTH: 901 base pairs
        ( B ) TYPE: nucleic acid
        ( C ) STRANDEDNESS: double
        ( D ) TOPOLOGY: linear (  i  i  ) MOLECULE TYPE: cDNA to mRNA (  v  i  ) ORIGINAL SOURCE:
        ( A ) ORGANISM: Homo sapiens
        ( F ) TISSUE TYPE: trachea (  x  i  ) SEQUENCE DESCRIPTION: SEQ ID NO:9:

| GAGGCTGAGG | AGGGAAGCTG | GCCGTGGCAA | GTCAGTCTGC | GGCTCAATAA | TGCCCACCAC | 60 |
|---|---|---|---|---|---|---|
| TGTGGAGGCA | GCCTGATCAA | TAACATGTGG | ATCCTGACAG | CAGCTCACTG | CTTCAGAAGC | 120 |
| AACTCTAATC | CTCGTGACTG | GATTGCCACG | TCTGGTATTT | CCACAACATT | TCCTAAACTA | 180 |
| AGAATGAGAG | TAAGAAATAT | TTTAATTCAT | AACAATTATA | AATCTGCAAC | TCATGAAAAT | 240 |
| GACATTGCAC | TTGTGAGACT | TGAGAACAGT | GTCACCTTTA | CCAAAGATAT | CCATAGTGTG | 300 |
| TGTCTCCCAG | CTGCTACCCA | GAATATTCCA | CCTGGCTCTA | CTGCTTATGT | AACAGGATGG | 360 |

```
GGCGCTCAAG AATATGCTGG CCACACAGTT CCAGAGCTAA GGCAAGGACA GGTCAGAATA    420

ATAAGTAATG ATGTATGTAA TGCACCACAT AGTTATAATG GAGCCATCTT GTCTGGAATG    480

CTGTGTGCTG GAGTACCTCA AGGTGGAGTG GACGCATGTC AGGGTGACTC TGGTGGCCCA    540

CTAGTACAAG AAGACTCACG GCGGCTTTGG TTTATTGTGG GGATAGTAAG CTGGGGAGAT    600

CAGTGTGGCC TGCCGGATAA GCCAGGAGTG TATACTCGAG TGACAGCCTA CCTTGACTGG    660

ATTAGGCAAC AAACTGGGAT CTAGTGCAAC AAGTGCATCC CTGTTGCAAA GTCTGTATGC    720

AGGTGTGCCT GTCTTAAATT CCAAAGCTTT ACATTTCAAC TGAAAAAGAA ACTAGAAATG    780

TCCTAATTTA ACATCTTGTT ACATAAATAT GGTTTAACAA ACACTGTTTA ACCTTTCTTT    840

ATTATTAAAG GTTTTCTATT TTCTCCAAAA AAAAAAAAA AAATCGATGT CGACTCGAGT    900

C                                                                   901
```

( 2 ) INFORMATION FOR SEQ ID NO:10:

( i ) SEQUENCE CHARACTERISTICS:
    ( A ) LENGTH: 25 bases
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO:10:

```
ACGTGGCAAT CCAGTCACGA GGATT                                          25
```

( 2 ) INFORMATION FOR SEQ ID NO:11:

( i ) SEQUENCE CHARACTERISTICS:
    ( A ) LENGTH: 25 bases
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO:11:

```
TGAGCTGCTG TCAGGATCCA CATGT                                          25
```

( 2 ) INFORMATION FOR SEQ ID NO:12:

( i ) SEQUENCE CHARACTERISTICS:
    ( A ) LENGTH: 35 bases
    ( B ) TYPE: nucleic acid
    ( C ) STRANDEDNESS: single
    ( D ) TOPOLOGY: linear ( i x ) FEATURE:
    ( A ) NAME/KEY:
    ( B ) LOCATION:
    ( C ) IDENTIFICATION METHOD:
    ( D ) OTHER INFORMATION: /note= "N = G modified with amino
      group"

( x i ) SEQUENCE DESCRIPTION: SEQ ID NO:12:

```
CACGAATTCA CTATCGATTC TGGAACCTTC AGAGN                               35
```

( 2 ) INFORMATION FOR SEQ ID NO:13:

( i ) SEQUENCE CHARACTERISTICS:
    ( A ) LENGTH: 38 bases
    ( B ) TYPE: nucleic acid
    ( C ) STRANDEDNESS: single
    ( D ) TOPOLOGY: linear ( x i ) SEQUENCE DESCRIPTION: SEQ ID NO:13:

| | | | |
|---|---|---|---|
| CTGGTTCGGC CCACCTCTGA AGGTTCCAGA ATCGATAG | | | 38 |

( 2 ) INFORMATION FOR SEQ ID NO:14:

( i ) SEQUENCE CHARACTERISTICS:
        ( A ) LENGTH: 789 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens
        ( F ) TISSUE TYPE: trachea ( x i ) SEQUENCE DESCRIPTION: SEQ ID NO:14:

```
CTGGTTCGGC   CCACCTCTGA   AGGTTCCAGA   ATCGATAGTG   AATTCGTGGA   GTGGGAATCT        60

CAAAGCAGTT   GAGTAGGCAG   AAAAAAGAAC   CTCTTCATTA   AGGATTAAAA   TGTATAGGCC       120

AGCACGTGTA   ACTTCGACTT   CAAGATTTCT   GAATCCATAT   GTAGTATGTT   TCATTGTCGT       180

CGCAGGGGTA   GTGATCCTGG   CAGTCACCAT   AGCTCTACTT   GTTACTTTT    TAGCTTTTGA       240

TCAAAAATCT   TACTTTTATA   GGAGCAGTTT   TCAACTCCTA   AATGTTGAAT   ATAATAGTCA       300

GTTAAATTCA   CCAGCTACAC   AGGAATACAG   GACTTTGAGT   GGAAGAATTG   AATCTCTGAT       360

TACTAAAACA   TTCAAAGAAT   CAAATTTAAG   AAATCAGTTC   ATCAGAGCTC   ATGTTGCCAA       420

ACTGAGGCAA   GATGGTAGTG   GTGTGAGAGC   GGATGTTGTC   ATGAAATTTC   AATTCACTAG       480

AAATAACAAT   GGAGCATCAA   TGAAAAGCAG   AATTGAGTCT   GTTTTACGAC   AAATGCTGAA       540

TAACTCTGGA   AACCTGGAAA   TAAACCCTTC   AACTGAGATA   ACATCACTTA   CTGACCAGGC       600

TGCAGCAAAT   TGGCTTATTA   ATGAATGTGG   GGCCGGTCCA   GACCTAATAA   CATTGTCTGA       660

GCAGAGAATC   CTTGGAGGCA   CTGAGGCTGA   GGAGGGAAGC   TGGCCGTGGC   AAGTCAGTCT       720

GCGGCTCAAT   AATGCCCACC   ACTGTGGAGG   CAGCCTGATC   AATAACATGT   GGATCCTGAC       780

AGCAGCTCA                                                                        789
```

( 2 ) INFORMATION FOR SEQ ID NO:15:

( i ) SEQUENCE CHARACTERISTICS:
        ( A ) LENGTH: 1517 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens
        ( F ) TISSUE TYPE: trachea ( x i ) SEQUENCE DESCRIPTION: SEQ ID NO:15:

```
                                                          GA  GTGGGAATCT          12

CAAAGCAGTT  GAGTAGGCAG  AAAAAAGAAC  CTCTTCATTA  AGGATTAAA  ATG  TAT  AGG           70
                                                           Met  Tyr  Arg
                                                                -185

CCA  GCA  CGT  GTA  ACT  TCG  ACT  TCA  AGA  TTT  CTG  AAT  CCA  TAT  GTA  GTA   118
Pro  Ala  Arg  Val  Thr  Ser  Thr  Ser  Arg  Phe  Leu  Asn  Pro  Tyr  Val  Val
          -180                    -175                         -170

TGT  TTC  ATT  GTC  GTC  GCA  GGG  GTA  GTG  ATC  CTG  GCA  GTC  ACC  ATA  GCT   166
Cys  Phe  Ile  Val  Val  Ala  Gly  Val  Val  Ile  Leu  Ala  Val  Thr  Ile  Ala
     -165                    -160                         -155
```

| | | | | | | | | | | | | | | | | |
|---|---|---|---|---|---|---|---|---|---|---|---|---|---|---|---|---|
| CTA | CTT | GTT | TAC | TTT | TTA | GCT | TTT | GAT | CAA | AAA | TCT | TAC | TTT | TAT | AGG | 214 |
| Leu | Leu | Val | Tyr | Phe | Leu | Ala | Phe | Asp | Gln | Lys | Ser | Tyr | Phe | Tyr | Arg | |
| -150 | | | | -145 | | | | | -140 | | | | | | | |
| AGC | AGT | TTT | CAA | CTC | CTA | AAT | GTT | GAA | TAT | AAT | AGT | CAG | TTA | AAT | TCA | 262 |
| Ser | Ser | Phe | Gln | Leu | Leu | Asn | Val | Glu | Tyr | Asn | Ser | Gln | Leu | Asn | Ser | |
| -135 | | | | -130 | | | | -125 | | | | | | -120 | | |
| CCA | GCT | ACA | CAG | GAA | TAC | AGG | ACT | TTG | AGT | GGA | AGA | ATT | GAA | TCT | CTG | 310 |
| Pro | Ala | Thr | Gln | Glu | Tyr | Arg | Thr | Leu | Ser | Gly | Arg | Ile | Glu | Ser | Leu | |
| | | | -115 | | | | -110 | | | | | | -105 | | | |
| ATT | ACT | AAA | ACA | TTC | AAA | GAA | TCA | AAT | TTA | AGA | AAT | CAG | TTC | ATC | AGA | 358 |
| Ile | Thr | Lys | Thr | Phe | Lys | Glu | Ser | Asn | Leu | Arg | Asn | Gln | Phe | Ile | Arg | |
| | | -100 | | | | -95 | | | | | | -90 | | | | |
| GCT | CAT | GTT | GCC | AAA | CTG | AGG | CAA | GAT | GGT | AGT | GGT | GTG | AGA | GCG | GAT | 406 |
| Ala | His | Val | Ala | Lys | Leu | Arg | Gln | Asp | Gly | Ser | Gly | Val | Arg | Ala | Asp | |
| | | -85 | | | | -80 | | | | -75 | | | | | | |
| GTT | GTC | ATG | AAA | TTT | CAA | TTC | ACT | AGA | AAT | AAC | AAT | GGA | GCA | TCA | ATG | 454 |
| Val | Val | Met | Lys | Phe | Gln | Phe | Thr | Arg | Asn | Asn | Asn | Gly | Ala | Ser | Met | |
| -70 | | | | | -65 | | | | | -60 | | | | | | |
| AAA | AGC | AGA | ATT | GAG | TCT | GTT | TTA | CGA | CAA | ATG | CTG | AAT | AAC | TCT | GGA | 502 |
| Lys | Ser | Arg | Ile | Glu | Ser | Val | Leu | Arg | Gln | Met | Leu | Asn | Asn | Ser | Gly | |
| -55 | | | | | -50 | | | | | -45 | | | | | -40 | |
| AAC | CTG | GAA | ATA | AAC | CCT | TCA | ACT | GAG | ATA | ACA | TCA | CTT | ACT | GAC | CAG | 550 |
| Asn | Leu | Glu | Ile | Asn | Pro | Ser | Thr | Glu | Ile | Thr | Ser | Leu | Thr | Asp | Gln | |
| | | | | -35 | | | | | -30 | | | | | | -25 | |
| GCT | GCA | GCA | AAT | TGG | CTT | ATT | AAT | GAA | TGT | GGG | GCC | GGT | CCA | GAC | CTA | 598 |
| Ala | Ala | Ala | Asn | Trp | Leu | Ile | Asn | Glu | Cys | Gly | Ala | Gly | Pro | Asp | Leu | |
| | | | -20 | | | | | -15 | | | | | | -10 | | |
| ATA | ACA | TTG | TCT | GAG | CAG | AGA | ATC | CTT | GGA | GGC | ACT | GAG | GCT | GAG | GAG | 646 |
| Ile | Thr | Leu | Ser | Glu | Gln | Arg | Ile | Leu | Gly | Gly | Thr | Glu | Ala | Glu | Glu | |
| | | | -5 | | | | 1 | | | | 5 | | | | | |
| GGA | AGC | TGG | CCG | TGG | CAA | GTC | AGT | CTG | CGG | CTC | AAT | AAT | GCC | CAC | CAC | 694 |
| Gly | Ser | Trp | Pro | Trp | Gln | Val | Ser | Leu | Arg | Leu | Asn | Asn | Ala | His | His | |
| 10 | | | | | 15 | | | | | 20 | | | | | 25 | |
| TGT | GGA | GGC | AGC | CTG | ATC | AAT | AAC | ATG | TGG | ATC | CTG | ACA | GCA | GCT | CAC | 742 |
| Cys | Gly | Gly | Ser | Leu | Ile | Asn | Asn | Met | Trp | Ile | Leu | Thr | Ala | Ala | His | |
| | | | | 30 | | | | | 35 | | | | | | 40 | |
| TGC | TTC | AGA | AGC | AAC | TCT | AAT | CCT | CGT | GAC | TGG | ATT | GCC | ACG | TCT | GGT | 790 |
| Cys | Phe | Arg | Ser | Asn | Ser | Asn | Pro | Arg | Asp | Trp | Ile | Ala | Thr | Ser | Gly | |
| | | | 45 | | | | | 50 | | | | | | 55 | | |
| ATT | TCC | ACA | ACA | TTT | CCT | AAA | CTA | AGA | ATG | AGA | GTA | AGA | AAT | ATT | TTA | 838 |
| Ile | Ser | Thr | Thr | Phe | Pro | Lys | Leu | Arg | Met | Arg | Val | Arg | Asn | Ile | Leu | |
| | | 60 | | | | | 65 | | | | | 70 | | | | |
| ATT | CAT | AAC | AAT | TAT | AAA | TCT | GCA | ACT | CAT | GAA | AAT | GAC | ATT | GCA | CTT | 886 |
| Ile | His | Asn | Asn | Tyr | Lys | Ser | Ala | Thr | His | Glu | Asn | Asp | Ile | Ala | Leu | |
| | 75 | | | | | 80 | | | | | 85 | | | | | |
| GTG | AGA | CTT | GAG | AAC | AGT | GTC | ACC | TTT | ACC | AAA | GAT | ATC | CAT | AGT | GTG | 934 |
| Val | Arg | Leu | Glu | Asn | Ser | Val | Thr | Phe | Thr | Lys | Asp | Ile | His | Ser | Val | |
| 90 | | | | | 95 | | | | | 100 | | | | | 105 | |
| TGT | CTC | CCA | GCT | GCT | ACC | CAG | AAT | ATT | CCA | CCT | GGC | TCT | ACT | GCT | TAT | 982 |
| Cys | Leu | Pro | Ala | Ala | Thr | Gln | Asn | Ile | Pro | Pro | Gly | Ser | Thr | Ala | Tyr | |
| | | | | 110 | | | | | 115 | | | | | 120 | | |
| GTA | ACA | GGA | TGG | GGC | GCT | CAA | GAA | TAT | GCT | GGC | CAC | ACA | GTT | CCA | GAG | 1030 |
| Val | Thr | Gly | Trp | Gly | Ala | Gln | Glu | Tyr | Ala | Gly | His | Thr | Val | Pro | Glu | |
| | | | 125 | | | | | 130 | | | | | 135 | | | |
| CTA | AGG | CAA | GGA | CAG | GTC | AGA | ATA | ATA | AGT | AAT | GAT | GTA | TGT | AAT | GCA | 1078 |
| Leu | Arg | Gln | Gly | Gln | Val | Arg | Ile | Ile | Ser | Asn | Asp | Val | Cys | Asn | Ala | |
| | | | 140 | | | | | 145 | | | | | 150 | | | |
| CCA | CAT | AGT | TAT | AAT | GGA | GCC | ATC | TTG | TCT | GGA | ATG | CTG | TGT | GCT | GGA | 1126 |
| Pro | His | Ser | Tyr | Asn | Gly | Ala | Ile | Leu | Ser | Gly | Met | Leu | Cys | Ala | Gly | |
| | 155 | | | | | 160 | | | | | 165 | | | | | |

-continued

| | | | | | | | | | | | | | | | | |
|---|---|---|---|---|---|---|---|---|---|---|---|---|---|---|---|---|
| GTA | CCT | CAA | GGT | GGA | GTG | GAC | GCA | TGT | CAG | GGT | GAC | TCT | GGT | GGC | CCA | 1174 |
| Val | Pro | Gln | Gly | Gly | Val | Asp | Ala | Cys | Gln | Gly | Asp | Ser | Gly | Gly | Pro | |
| 170 | | | | | 175 | | | | 180 | | | | | | 185 | |
| CTA | GTA | CAA | GAA | GAC | TCA | CGG | CGG | CTT | TGG | TTT | ATT | GTG | GGG | ATA | GTA | 1222 |
| Leu | Val | Gln | Glu | Asp | Ser | Arg | Arg | Leu | Trp | Phe | Ile | Val | Gly | Ile | Val | |
| | | | | 190 | | | | | 195 | | | | | 200 | | |
| AGC | TGG | GGA | GAT | CAG | TGT | GGC | CTG | CCG | GAT | AAG | CCA | GGA | GTG | TAT | ACT | 1270 |
| Ser | Trp | Gly | Asp | Gln | Cys | Gly | Leu | Pro | Asp | Lys | Pro | Gly | Val | Tyr | Thr | |
| | | | | 205 | | | | | 210 | | | | | 215 | | |
| CGA | GTG | ACA | GCC | TAC | CTT | GAC | TGG | ATT | AGG | CAA | CAA | ACT | GGG | ATC | | 1315 |
| Arg | Val | Thr | Ala | Tyr | Leu | Asp | Trp | Ile | Arg | Gln | Gln | Thr | Gly | Ile | | |
| | | 220 | | | | | 225 | | | | | 230 | | | | |

| | | | | |
|---|---|---|---|---|
| TAGTGCAACA | AGTGCATCCC | TGTTGCAAAG | TCTGTATGCA | GGTGTGCCTG | TCTTAAATTC | 1375 |
| CAAAGCTTTA | CATTTCAACT | GAAAAAGAAA | CTAGAAATGT | CCTAATTTAA | CATCTTGTTA | 1435 |
| CATAAATATG | GTTAACAAA | CACTGTTTAA | CCTTTCTTTA | TTATTAAAGG | TTTTCTATTT | 1495 |
| TCTCCAAAAA | AAAAAAAAA | AA | | | | 1517 |

( 2 ) INFORMATION FOR SEQ ID NO:16:

( i ) SEQUENCE CHARACTERISTICS:
    ( A ) LENGTH: 10241 base pairs
    ( B ) TYPE: nucleic acid
    ( C ) STRANDEDNESS: double
    ( D ) TOPOLOGY: cyclic ( i i ) MOLECULE TYPE: other nucleic acid (vector DNA)

( x i ) SEQUENCE DESCRIPTION: SEQ ID NO:16:

| | | | | | |
|---|---|---|---|---|---|
| GCAGTTCGTT | GACGCCTTCC | TCCGTGTGGC | CGAACACGTC | GAGCGGGTGG | TCGATGACCA | 60 |
| GCGGCGTGCC | GCACGCGACG | CACAAGTATC | TGTACACCGA | ATGATCGTCG | GGCGAAGGCA | 120 |
| CGTCGGCCTC | CAAGTGGCAA | TATTGGCAAA | TTCGAAAATA | TATACAGTTG | GGTTGTTTGC | 180 |
| GCATATCTAT | CGTGGCGTTG | GGCATGTACG | TCCGAACGTT | GATTTGCATG | CAAGCCGAAA | 240 |
| TTAAATCATT | GCGATTAGTG | CGATTAAAAC | GTTGTACATC | CTCGCTTTTA | ATCATGCCGT | 300 |
| CGATTAAATC | GCGCAATCGA | GTCAAGTGAT | CAAAGTGTGG | AATAATGTTT | TCTTTGTATT | 360 |
| CCCGAGTCAA | GCGCAGCGCG | TATTTAACA | AACTAGCCAT | CTTGTAAGTT | AGTTTCATTT | 420 |
| AATGCAACTT | TATCCAATAA | TATATTATGT | ATCGCACGTC | AAGAATTAAC | AATGCGCCCG | 480 |
| TTGTCGCATC | TCAACACGAC | TATGATAGAG | ATCAAATAAA | GCGCGAATTA | AATAGCTTGC | 540 |
| GACGCAACGT | GCACGATCTG | TGCACGCGTT | CCGGCACGAG | CTTTGATTGT | AATAAGTTTT | 600 |
| TACGAAGCGA | TGACATGACC | CCCGTAGTGA | CAACGATCAC | GCCCAAAAGA | ACTGCCGACT | 660 |
| ACAAAATTAC | CGAGTATGTC | GGTGACGTTA | AAACTATTAA | GCCATCCAAT | CGACCGTTAG | 720 |
| TCGAATCAGG | ACCGCTGGTG | CGAGAAGCCG | CGAAGTATGG | CGAATGCATC | GTATAACGTG | 780 |
| TGGAGTCCGC | TCATTAGAGC | GTCATGTTTA | GACAAGAAAG | CTACATATTT | AATTGATCCC | 840 |
| GATGATTTTA | TTGATAAATT | GACCCTAACT | CCATACACGG | TATTCTACAA | TGGCGGGGTT | 900 |
| TTGGTCAAAA | TTTCCGGACT | GCGATTGTAC | ATGCTGTTAA | CGGCTCCGCC | CACTATTAAT | 960 |
| GAAATTAAAA | ATTCCAATTT | TAAAAAACGC | AGCAAGAGAA | ACATTTGTAT | GAAAGAATGC | 1020 |
| GTAGAAGGAA | AGAAAAATGT | CGTCGACATG | CTGAACAACA | AGATTAATAT | GCCTCCGTGT | 1080 |
| ATAAAAAAAA | TATTGAACGA | TTTGAAAGAA | AACAATGTAC | CGCGCGGCGG | TATGTACAGG | 1140 |
| AAGAGGTTTA | TACTAAACTG | TTACATTGCA | AACGTGGTTT | CGTGTGCCAA | GTGTGAAAAC | 1200 |
| CGATGTTTAA | TCAAGGCTCT | GACGCATTTC | TACAACCACG | ACTCCAAGTG | TGTGGGTGAA | 1260 |
| GTCATGCATC | TTTTAATCAA | ATCCCAAGAT | GTGTATAAAC | CACCAAACTG | CCAAAAAATG | 1320 |

```
AAAACTGTCG ACAAGCTCTG TCCGTTTGCT GGCAACTGCA AGGGTCTCAA TCCTATTTGT    1380
AATTATTGAA TAATAAAACA ATTATAAATG CTAAATTTGT TTTTTATTAA CGATACAAAC    1440
CAAACGCAAC AAGAACATTT GTAGTATTAT CTATAATTGA AAACGCGTAG TTATAATCGC    1500
TGAGGTAATA TTTAAAATCA TTTTCAAATG ATTCACAGTT AATTGCGAC AATATAATTT     1560
TATTTTCACA TAAACTAGAC GCCTTGTCGT CTTCTTCTTC GTATTCCTTC TCTTTTTCAT    1620
TTTTCTCCTC ATAAAAATTA ACATAGTTAT TATCGTATCC ATATATGTAT CTATCGTATA    1680
GAGTAAATTT TTTGTTGTCA TAAATATATA TGTCTTTTTT AATGGGGTGT ATAGTACCGC    1740
TGCGCATAGT TTTTCTGTAA TTTACAACAG TGCTATTTTC TGGTAGTTCT TCGGAGTGTG    1800
TTGCTTTAAT TATTAAATTT ATATAATCAA TGAATTTGGG ATCGTCGGTT TTGTACAATA    1860
TGTTGCCGGC ATAGTACGCA GCTTCTTCTA GTTCAATTAC ACCATTTTTT AGCAGCACCG    1920
GATTAACATA ACTTCCAAA ATGTTGTACG AACCGTTAAA CAAAAACAGT TCACCTCCCT     1980
TTTCTATACT ATTGTCTGCG AGCAGTTGTT TGTTGTTAAA ATAACAGCC ATTGTAATGA     2040
GACGCACAAA CTAATATCAC AAACTGGAAA TGTCTATCAA TATATAGTTG CTGATATCAG    2100
ATCCAGACAT GATAAGATAC ATTGATGAGT TTGGACAAAC CACAACTAGA ATGCAGTGAA    2160
AAAAATGCTT TATTTGTGAA ATTTGTGATG CTATTGCTTT ATTTGTAACC ATTATAAGCT    2220
GCAATAAACA AGTTAACAAC AACAATTGCA TTCATTTTAT GTTTCAGGTT CAGGGGGAGG    2280
TGTGGGAGGT TTTTTAAAGC AAGTAAAACC TCTACAAATG TGGTATGGCT GATTATGATC    2340
CTCTAGAGTC GAGATCCCCC TCGCCCGGTT ATTATTATTT TTGACACCAG ACCAACTGGT    2400
AATGGTAGCG ACCGGCGCTC AGCTGGAATT CCGCCGATAC TGACGGGCTC CAGGAGTCGT    2460
CGCCACCAAT CCCCATATGG AAACCGTCGA TATTCAGCCA TGTGCCTTCT TCCGCGTGCA    2520
GCAGATGGCG ATGGCTGGTT TCCATCAGTT GCTGTTGACT GTAGCGGCTG ATGTTGAACT    2580
GGAAGTCGCC GCGCCACTGG TGTGGGCCAT AATTCAATTC GCGCGTCCCG CAGCGCAGAC    2640
CGTTTTCGCT CGGGAAGACG TACGGGGTAT ACATGTCTGA CAATGGCAGA TCCCAGCGGT    2700
CAAAACAGGC GGCAGTAAGG CGGTCGGGAT AGTTTTCTTG CGGCCCTAAT CCGAGCCAGT    2760
TTACCCGCTC TGCTACCTGC GCCAGCTGGC AGTTCAGGCC AATCCGCGCC GGATGCGGTG    2820
TATCGCTCGC CACTTCAACA TCAACGGTAA TCGCCATTTG ACCACTACCA TCAATCCGGT    2880
AGGTTTTCCG GCTGATAAAT AAGGTTTTCC CCTGATGCTG CCACGCGTGA GCGGTCGTAA    2940
TCAGCACCGC ATCAGCAAGT GTATCTGCCG TGCACTGCAA CAACGCTGCT TCGGCCTGGT    3000
AATGGCCCGC CGCCTTCCAG CGTTCGACCC AGGCGTTAGG GTCAATGCGG GTCGCTTCAC    3060
TTACGCCAAT GTCGTTATCC AGCGGTGCAC GGGTGAACTG ATCGCGCAGC GGCGTCAGCA    3120
GTTGTTTTTT ATCGCCAATC CACATCTGTG AAAGAAAGCC TGACTGGCGG TTAAATTGCC    3180
AACGCTTATT ACCCAGCTCG ATGCAAAAAT CCATTTCGCT GGTGGTCAGA TGCGGGATGG    3240
CGTGGGACGC GGCGGGGAGC GTCACACTGA GGTTTTCCGC CAGACGCCAC TGCTGCCAGG    3300
CGCTGATGTG CCCGGCTTCT GACCATGCGG TCGCGTTCGG TTGCACTACG CGTACTGTGA    3360
GCCAGAGTTG CCCGGCGCTC TCCGGCTGCG GTAGTTCAGG CAGTTCAATC AACTGTTTAC    3420
CTTGTGGAGC GACATCCAGA GGCACTTCAC CGCTTGCCAG CGGCTTACCA TCCAGCGCCA    3480
CCATCCAGTG CAGGAGCTCG TTATCGCTAT GACGGAACAG GTATTCGCTG GTCACTTCGA    3540
TGGTTTGCCC GGATAAACGG AACTGGAAAA ACTGCTGCTG GTGTTTGCT TCCGTCAGCG     3600
CTGGATGCGG CGTGCGGTCG GCAAAGACCA GACCGTTCAT ACAGAACTGG CGATCGTTCG    3660
GCGTATCGCC AAAATCACCG CCGTAAGCCG ACCACGGGTT GCCGTTTTCA TCATATTTAA    3720
```

-continued

```
TCAGCGACTG ATCCACCCAG TCCCAGACGA AGCCGCCCTG TAAACGGGGA TACTGACGAA    3780
ACGCCTGCCA GTATTTAGCG AAACCGCCAA GACTGTTACC CATCGCGTGG GCGTATTCGC    3840
AAAGGATCAG CGGGCGCGTC TCTCCAGGTA GCGAAAGCCA TTTTTTGATG GACCATTTCG    3900
GCACAGCCGG GAAGGGCTGG TCTTCATCCA CGCGCGCGTA CATCGGGCAA ATAATATCGG    3960
TGGCCGTGGT GTCGGCTCCG CCGCCTTCAT ACTGCACCGG GCGGGAAGGA TCGACAGATT    4020
TGATCCAGCG ATACAGCGCG TCGTGATTAG CGCCGTGGCC TGATTCATTC CCCAGCGACC    4080
AGATGATCAC ACTCGGGTGA TTACGATCGC GCTGCACCAT TCGCGTTACG CGTTCGCTCA    4140
TCGCCGGTAG CCAGCGCGGA TCATCGGTCA GACGATTCAT TGGCACCATG CCGTGGGTTT    4200
CAATATTGGC TTCATCCACC ACATACAGGC CGTAGCGGTC GCACAGCGTG TACCACAGCG    4260
GATGGTTCGG ATAATGCGAA CAGCGCACGG CGTTAAAGTT GTTCTGCTTC ATCAGCAGGA    4320
TATCCTGCAC CATCGTCTGC TCATCCATGA CCTGACCATG CAGAGGATGA TGCTCGTGAC    4380
GGTTAACGCC TCGAATCAGC AACGGCTTGC CGTTCAGCAG CAGCAGACCA TTTTCAATCC    4440
GCACCTCGCG GAAACCGACA TCGCAGGCTT CTGCTTCAAT CAGCGTGCCG TCGGCGGTGT    4500
GCAGTTCAAC CACCGCACGA TAGAGATTCG GGATTTCGGC GCTCCACAGT TTCGGGTTTT    4560
CGACGTTCAG ACGTAGTGTG ACGCGATCGG CATAACCACC ACGCTCATCG ATAATTTCAC    4620
CGCCGAAAGG CGCGGTGCCG CTGGCGACCT GCGTTTCACC CTGCCATAAA GAAACTGTTA    4680
CCCGTAGGTA GTCACGCAAC TCGCCGCACA TCTGAACTTC AGCCTCCAGT ACAGCGCGGC    4740
TGAAATCATC ATTAAAGCGA GTGGCAACAT GGAAATCGCT GATTTGTGTA GTCGGTTTAT    4800
GCAGCAACGA GACGTCACGG AAAATGCCGC TCATCCGCCA CATATCCTGA TCTTCCAGAT    4860
AACTGCCGTC ACTCCAACGC AGCACCATCA CCGCGAGGCG GTTTTCTCCG GCGCGTAAAA    4920
ATGCGCTCAG GTCAAATTCA GACGGCAAAC GACTGTCCTG GCCGTAACCG ACCCAGCGCC    4980
CGTTGCACCA CAGATGAAAC GCCGAGTTAA CGCCATCAAA ATAATTCGC GTCTGGCCTT     5040
CCTGTAGCCA GCTTTCATCA ACATTAAATG TGAGCGAGTA ACAACCCGTC GGATTCTCCG    5100
TGGGAACAAA CGGCGGATTG ACCGTAATGG GATAGGTTAC GTTGGTGTAG ATGGGCGCAT    5160
CGTAACCGTG CATCTGCCAG TTTGAGGGGA CGACGACAGT ATCGGCCTCA GGAAGATCGC    5220
ACTCCAGCCA GCTTTCCGGC ACCGCTTCTG GTGCCGGAAA CCAGGCAAAG CGCCATTCGC    5280
CATTCAGGCT GCGCAACTGT TGGGAAGGGC GATCGGTGCG GGCCTCTTCG CTATTACGCC    5340
AGCTGGCGAA AGGGGGATGT GCTGCAAGGC GATTAAGTTG GGTAACGCCA GGGTTTTCCC    5400
AGTCACGACG TTGTAAAACG ACGGGATCTA TCATTTTTAG CAGTGATTCT AATTGCAGCT    5460
GCTCTTTGAT ACAACTAATT TTACGACGAC GATGCGAGCT TTTATTCAAC CGAGCGTGCA    5520
TGTTTGCAAT CGTGCAAGCG TTATCAATTT TTCATTATCG TATTGTTGCA CATCAACAGG    5580
CTGGACACCA CGTTGAACTC GCCGCAGTTT TGCGGCAAGT TGGACCCGCC GCGCATCCAA    5640
TGCAAACTTT CCGACATTCT GTTGCCTACG AACGATTGAT TCTTTGTCCA TTGATCGAAG    5700
CGAGTGCCTT CGACTTTTTC GTGTCCAGTG TGGCTTGATA TCATGGAGAT AATTAAAATG    5760
ATAACCATCT CGCAAATAAA TAAGTATTTT ACTGTTTTCG TAACAGTTTT GTAATAAAAA    5820
AACCTATAAA TATTCCGGAT TATTCATACC GTCCACCAT CGGGCGTGCT AGCGGATCCG     5880
AGCTCGAGAT CTGCAGCTGG TACCATGGAA TTCGAAGCTT GTCGTTGGAT GGAAAGGAAA    5940
AGAGTTCTAC AGGGAAACTT GGACCCGCTT CATGGAAGAC AGCTTCCCCA TTGTTAACGA    6000
CCAAGAAGTG ATGGATGTTT TCCTTGTTGT CAACATGCGT CCCACTAGAC CAACCGTTG    6060
TTACAAATTC CTGGCCCAAC ACGCTCTGCG TTGCGACCCC GACTATGTAC CTCATGACGT    6120
```

-continued

```
GATTAGGATC GTCGAGCCTT CATGGGTGGG CAGCAACAAC GAGTACCGCA TCAGCCTGGC      6180

TAAGAAGGGC GGCGGCTGCC CAATAATGAA CCTTCACTCT GAGTACACCA ACTCGTTCGA      6240

ACAGTTCATC GATCGTGTCA TCTGGGAGAA CTTCTACAAG CCCATCGTTT ACATCGGTAC      6300

CGACTCTGCT GAAGAGGAGG AAATTCTCCT TGAAGTTTCC CTGGTGTTCA AAGTAAAGGA      6360

GTTTGCACCA GACGCACCTC TGTTCACTGG TCCGGCGTAT TAAAACACGA TACATTGTTA      6420

TTAGTACATT TATTAAGCGC TAGATTCTGT GCGTTGTTGA TTTACAGACA ATTGTTGTAC      6480

GTATTTTAAT AATTCATTAA ATTTATAATC TTTAGGGTGG TATGTTAGAG CGAAAATCAA      6540

ATGATTTTCA GCGTCTTTAT ATCTGAATTT AAATATTAAA TCCTCAATAG ATTTGTAAAA      6600

TAGGTTTCGA TTAGTTTCAA ACAAGGGTTG TTTTTCCGAA CCGATGGCTG GACTATCTAA      6660

TGGATTTTCG CTCAACGCCA CAAAACTTGC CAAATCTTGT AGCAGCAATC TAGCTTTGTC      6720

GATATTCGTT TGTGTTTTGT TTGTAATAA AGGTTCGACG TCGTTCAAAA TATTATGCGC      6780

TTTTGTATTT CTTTCATCAC TGTCGTTAGT GTACAATTGA CTCGACGTAA ACACGTTAAA      6840

TAAAGCTAGC TTGGACATAT TTAACATCGG GCGTGTTAGC TTTATTAGGC CGATTATCGT      6900

CGTCGTCCCA ACCCTCGTCG TTAGAAGTTG CTTCCGAAGA CGATTTTGCC ATAGCCACAC      6960

GACGCCTATT AATTGTGTCG GCTAACACGT CCGCGATCAA ATTTGTAGTT GAGCTTTTTG      7020

GAATTATTTC TGATTGCGGG CGTTTTTGGG CGGGTTTCAA TCTAACTGTG CCCGATTTTA      7080

ATTCAGACAA CACGTTAGAA AGCGATGGTG CAGGCGGTGG TAACATTTCA GACGGCAAAT      7140

CTACTAATGG CGGCGGTGGT GGAGCTGATG ATAAATCTAC CATCGGTGGA GGCGCAGGCG      7200

GGGCTGGCGG CGGAGGCGGA GGCGGAGGTG GTGGCGGTGA TGCAGACGGC GGTTTAGGCT      7260

CAAATGTCTC TTTAGGCAAC ACAGTCGGCA CCTCAACTAT TGTACTGGTT TCGGGCGCCG      7320

TTTTGGTTT GACCGGTCTG AGACGAGTGC GATTTTTTC GTTTCTAATA GCTTCCAACA      7380

ATTGTTGTCT GTCGTCTAAA GGTGCAGCGG GTTGAGGTTC CGTCGGCATT GGTGGAGCGG      7440

GCGGCAATTC AGACATCGAT GGTGGTGGTG GTGGTGGAGG CGCTGGAATG TTAGGCACGG      7500

GAGAAGGTGG TGGCGGCGGT GCCGCCGGTA TAATTTGTTC TGGTTTAGTT TGTTCGCGCA      7560

CGATTGTGGG CACCGGCGCA GGCGCCGCTG GCTGCACAAC GGAAGGTCGT CTGCTTCGAG      7620

GCAGCGCTTG GGGTGGTGGC AATTCAATAT TATAATTGGA ATACAAATCG TAAAAATCTG      7680

CTATAAGCAT TGTAATTTCG CTATCGTTTA CCGTGCCGAT ATTTAACAAC CGCTCAATGT      7740

AAGCAATTGT ATTGTAAAGA GATTGTCTCA AGCTCCGCAC GCCGATAACA AGCCTTTTCA      7800

TTTTTACTAC AGCATTGTAG TGGCGAGACA CTTCGCTGTC GTCGACTCGA GTTCTATAGT      7860

GTCACCTAAA TCGTATGTGT ATGATACATA AGGTTATGTA TTAATTGTAG CCGCGTTCTA      7920

ACGACAATAT GTCCATATGG TGCACTCTCA GTACAATCTG CTCTGATGCC GCATAGTTAA      7980

GCCAGCCCCG ACACCCGCCA ACACCCGCTG ACGCGCCCTG ACGGGCTTGT CTGCTCCCGG      8040

CATCCGCTTA CAGACAAGCT GTGACCGTCT CCGGGAGCTG CATGTGTCAG AGGTTTTCAC      8100

CGTCATCACC GAAACGCGCG AGAGGAAAGG GCCTCGTGAT ACGCCTATTT TTATAGGTTA      8160

ATGTCATGAT AATAATGGTT TCTTAGACGT CAGGTGGCAC TTTTCGGGGA AATGTGCGCG      8220

GAACCCCTAT TTGTTTATTT TTCTAAATAC ATTCAAATAT GTATCCGCTC ATGAGACAAT      8280

AACCCTGATA AATGCTTCAA TAATATTGAA AAAGGAAGAG TATGAGTATT CAACATTTCC      8340

GTGTCGCCCT TATTCCCTTT TTTGCGGCAT TTTGCCTTCC TGTTTTTGCT CACCCAGAAA      8400

CGCTGGTGAA AGTAAAAGAT GCTGAAGATC AGTTGGGTGC ACGAGTGGGT TACATCGAAC      8460

TGGATCTCAA CAGCGGTAAG ATCCTTGAGA GTTTTCGCCC CGAAGAACGT TTTCCAATGA      8520
```

| | | | | | | |
|---|---|---|---|---|---|---|
| TGAGCACTTT | TAAAGTTCTG | CTATGTGGCG | CGGTATTATC | CCGTATTGAC | GCCGGGCAAG | 8580 |
| AGCAACTCGG | TCGCCGCATA | CACTATTCTC | AGAATGACTT | GGTTGAGTAC | TCACCAGTCA | 8640 |
| CAGAAAAGCA | TCTTACGGAT | GGCATGACAG | TAAGAGAATT | ATGCAGTGCT | GCCATAACCA | 8700 |
| TGAGTGATAA | CACTGCGGCC | AACTTACTTC | TGACAACGAT | CGGAGGACCG | AAGGAGCTAA | 8760 |
| CCGCTTTTTT | GCACAACATG | GGGGATCATG | TAACTCGCCT | TGATCGTTGG | GAACCGGAGC | 8820 |
| TGAATGAAGC | CATACCAAAC | GACGAGCGTG | ACACCACGAT | GCCTGTAGCA | ATGGCAACAA | 8880 |
| CGTTGCGCAA | ACTATTAACT | GGCGAACTAC | TTACTCTAGC | TTCCGGCAA | CAATTAATAG | 8940 |
| ACTGGATGGA | GGCGGATAAA | GTTGCAGGAC | CACTTCTGCG | CTCGGCCCTT | CCGGCTGGCT | 9000 |
| GGTTTATTGC | TGATAAATCT | GGAGCCGGTG | AGCGTGGGTC | TCGCGGTATC | ATTGCAGCAC | 9060 |
| TGGGGCCAGA | TGGTAAGCCC | TCCCGTATCG | TAGTTATCTA | CACGACGGGG | AGTCAGGCAA | 9120 |
| CTATGGATGA | ACGAAATAGA | CAGATCGCTG | AGATAGGTGC | CTCACTGATT | AAGCATTGGT | 9180 |
| AACTGTCAGA | CCAAGTTTAC | TCATATATAC | TTTAGATTGA | TTTAAAACTT | CATTTTTAAT | 9240 |
| TTAAAGGAT | CTAGGTGAAG | ATCCTTTTG | ATAATCTCAT | GACCAAAATC | CCTTAACGTG | 9300 |
| AGTTTTCGTT | CCACTGAGCG | TCAGACCCCG | TAGAAAAGAT | CAAAGGATCT | TCTTGAGATC | 9360 |
| CTTTTTTTCT | GCGCGTAATC | TGCTGCTTGC | AAACAAAAAA | ACCACCGCTA | CCAGCGGTGG | 9420 |
| TTTGTTTGCC | GGATCAAGAG | CTACCAACTC | TTTTTCCGAA | GGTAACTGGC | TTCAGCAGAG | 9480 |
| CGCAGATACC | AAATACTGTC | CTTCTAGTGT | AGCCGTAGTT | AGGCCACCAC | TTCAAGAACT | 9540 |
| CTGTAGCACC | GCCTACATAC | CTCGCTCTGC | TAATCCTGTT | ACCAGTGGCT | GCTGCCAGTG | 9600 |
| GCGATAAGTC | GTGTCTTACC | GGGTTGGACT | CAAGACGATA | GTTACCGGAT | AAGGCGCAGC | 9660 |
| GGTCGGGCTG | AACGGGGGGT | TCGTGCACAC | AGCCCAGCTT | GGAGCGAACG | ACCTACACCG | 9720 |
| AACTGAGATA | CCTACAGCGT | GAGCATTGAG | AAAGCGCCAC | GCTTCCCGAA | GGGAGAAAGG | 9780 |
| CGGACAGGTA | TCCGGTAAGC | GGCAGGGTCG | GAACAGGAGA | GCGCACGAGG | GAGCTTCCAG | 9840 |
| GGGGAAACGC | CTGGTATCTT | TATAGTCCTG | TCGGGTTTCG | CCACCTCTGA | CTTGAGCGTC | 9900 |
| GATTTTTGTG | ATGCTCGTCA | GGGGGGCGGA | GCCTATGGAA | AAACGCCAGC | AACGCGGCCT | 9960 |
| TTTTACGGTT | CCTGGCCTTT | TGCTGGCCTT | TTGCTCACAT | GTTCTTTCCT | GCGTTATCCC | 10020 |
| CTGATTCTGT | GGATAACCGT | ATTACCGCCT | TTGAGTGAGC | TGATACCGCT | CGCCGCAGCC | 10080 |
| GAACGACCGA | GCGCAGCGAG | TCAGTGAGCG | AGGAAGCGGA | AGAGCGCCCA | ATACGCAAAC | 10140 |
| CGCCTCTCCC | CGCGCGTTGG | CCGATTCATT | AATGCAGGTT | AACCTGGCTT | ATCGAAATTA | 10200 |
| ATACGACTCA | CTATAGGGAG | ACCGGCAGAT | CGATCTGTCG | A | | 10241 |

( 2 ) INFORMATION FOR SEQ ID NO:17:

( i ) SEQUENCE CHARACTERISTICS:
        ( A ) LENGTH: 53 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:17:

| | | | | | |
|---|---|---|---|---|---|
| GATCCATGTA | TAGGCCAGCA | CGTGTAACTT | CGACTTCAAG | ATTTCTGAAT | CCA | 53 |

( 2 ) INFORMATION FOR SEQ ID NO:18:

( i ) SEQUENCE CHARACTERISTICS:
        ( A ) LENGTH: 51 bases
        ( B ) TYPE: nucleic acid ( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:18:

TATGGATTCA GAAATCTTGA AGTCGAAGTT ACACGTGCTG GCCTATACAT G        51

( 2 ) INFORMATION FOR SEQ ID NO:19:

( i ) SEQUENCE CHARACTERISTICS:
( A ) LENGTH: 232 amino acids
( B ) TYPE: amino acid
( C ) STRANDEDNESS: single
( D ) TOPOLOGY: linear ( x i ) SEQUENCE DESCRIPTION: SEQ ID NO:19:

| Ile | Leu | Gly | Gly | Thr | Glu | Ala | Glu | Glu | Gly | Ser | Trp | Pro | Trp | Gln | Val |
|---|---|---|---|---|---|---|---|---|---|---|---|---|---|---|---|
| 1 | | | | 5 | | | | | 10 | | | | | 15 | |
| Ser | Leu | Arg | Leu | Asn | Asn | Ala | His | His | Cys | Gly | Gly | Ser | Leu | Ile | Asn |
| | | | 20 | | | | | 25 | | | | | 30 | | |
| Asn | Met | Trp | Ile | Leu | Thr | Ala | Ala | His | Cys | Phe | Arg | Ser | Asn | Ser | Asn |
| | | 35 | | | | | 40 | | | | | 45 | | | |
| Pro | Arg | Asp | Trp | Ile | Ala | Thr | Ser | Gly | Ile | Ser | Thr | Thr | Phe | Pro | Lys |
| | 50 | | | | | 55 | | | | | 60 | | | | |
| Leu | Arg | Met | Arg | Val | Arg | Asn | Ile | Leu | Ile | His | Asn | Asn | Tyr | Lys | Ser |
| 65 | | | | | 70 | | | | | 75 | | | | | 80 |
| Ala | Thr | His | Glu | Asn | Asp | Ile | Ala | Leu | Val | Arg | Leu | Glu | Asn | Ser | Val |
| | | | | 85 | | | | | 90 | | | | | 95 | |
| Thr | Phe | Thr | Lys | Asp | Ile | His | Ser | Val | Cys | Leu | Pro | Ala | Ala | Thr | Gln |
| | | | 100 | | | | | 105 | | | | | 110 | | |
| Asn | Ile | Pro | Pro | Gly | Ser | Thr | Ala | Tyr | Val | Thr | Gly | Trp | Gly | Ala | Gln |
| | | | 115 | | | | | 120 | | | | | 125 | | |
| Glu | Tyr | Ala | Gly | His | Thr | Val | Pro | Glu | Leu | Arg | Gln | Gly | Gln | Val | Arg |
| | | 130 | | | | | 135 | | | | | 140 | | | |
| Ile | Ile | Ser | Asn | Asp | Val | Cys | Asn | Ala | Pro | His | Ser | Tyr | Asn | Gly | Ala |
| 145 | | | | | 150 | | | | | 155 | | | | | 160 |
| Ile | Leu | Ser | Gly | Met | Leu | Cys | Ala | Gly | Val | Pro | Gln | Gly | Gly | Val | Asp |
| | | | | 165 | | | | | 170 | | | | | 175 | |
| Ala | Cys | Gln | Gly | Asp | Ser | Gly | Gly | Pro | Leu | Val | Gln | Glu | Asp | Ser | Arg |
| | | | 180 | | | | | 185 | | | | | 190 | | |
| Arg | Leu | Trp | Phe | Ile | Val | Gly | Ile | Val | Ser | Trp | Gly | Asp | Gln | Cys | Gly |
| | | | 195 | | | | 200 | | | | | 205 | | | |
| Leu | Pro | Asp | Lys | Pro | Gly | Val | Tyr | Thr | Arg | Val | Thr | Ala | Tyr | Leu | Asp |
| | | 210 | | | | | 215 | | | | | 220 | | | |
| Trp | Ile | Arg | Gln | Gln | Thr | Gly | Ile | | | | | | | | |
| 225 | | | | | 230 | | | | | | | | | | |

( 2 ) INFORMATION FOR SEQ ID NO:20:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i x ) FEATURE:
( A ) NAME/KEY:
( B ) LOCATION:
( C ) IDENTIFICATION METHOD:
( D ) OTHER INFORMATION: /note= "Xaa at position 1 is Boc-Ile
and Xaa at position 4 is Arg-MCA"

( x i ) SEQUENCE DESCRIPTION: SEQ ID NO:20:

Xaa Gln Gly Xaa
1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION: /note= "Xaa at position 1 is Suc-Ala
            and Xaa at position 4 is Phe-MCA"

( x i ) SEQUENCE DESCRIPTION: SEQ ID NO:21:

Xaa Ala Pro Xaa
1

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION: /note= "Xaa at position 1 is Suc-Gly
            and Xaa at position 5 is Pro-MCA"

( x i ) SEQUENCE DESCRIPTION: SEQ ID NO:22:

Xaa Pro Leu Gly Xaa
1                5

( 2 ) INFORMATION FOR SEQ ID NO:23:

( i ) SEQUENCE CHARACTERISTICS:
        ( A ) LENGTH: 696 bases
        ( B ) TYPE: nucleic acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION: /note= "N = T or U"

( x i ) SEQUENCE DESCRIPTION: SEQ ID NO:23:

```
ANC  CNN  GGA  GGC  ACN  GAG  GCN  GAG  GAG  GGA  AGC  NGG  CCG  NGG  CAA  GNC       48

AGN  CNG  CGG  CNC  AAN  AAN  GCC  CAC  CAC  NGN  GGA  GGC  AGC  CNG  ANC  AAN       96

AAC  ANG  NGG  ANC  CNG  ACA  GCA  GCN  CAC  NGC  NNC  AGA  AGC  AAC  NCN  AAN      144

CCN  CGN  GAC  NGG  ANN  GCC  ACG  NCN  GGN  ANN  NCC  ACA  ACA  NNN  CCN  AAA      192

CNA  AGA  ANG  AGA  GNA  AGA  AAN  ANN  NNA  ANN  CAN  AAC  AAN  NAN  AAA  NCN      240

GCA  ACN  CAN  GAA  AAN  GAC  ANN  GCA  CNN  GNG  AGA  CNN  GAG  AAC  AGN  GNC      288

ACC  NNN  ACC  AAA  GAN  ANC  CAN  AGN  GNG  NGN  CNC  CCA  GCN  GCN  ACC  CAG      336

AAN  ANN  CCA  CCN  GGC  NCN  ACN  GCN  NAN  GNA  ACA  GGA  NGG  GGC  GCN  CAA      384
```

|  |  |  |  |  |  |  |  |  |  |  |  |  |  |  |  |
|--|--|--|--|--|--|--|--|--|--|--|--|--|--|--|--|
| GAA | NAN | GCN | GGC | CAC | ACA | GNN | CCA | GAG | CNA | AGG | CAA | GGA | CAG | GNC | AGA | 432 |
| ANA | ANA | AGN | AAN | GAN | GNA | NGN | AAN | GCA | CCA | CAN | AGN | NAN | AAN | GGA | GCC | 480 |
| ANC | NNG | NCN | GGA | ANG | CNG | NGN | GCN | GGA | GNA | CCN | CAA | GGN | GGA | GNG | GAC | 528 |
| GCA | NGN | CAG | GGN | GAC | NCN | GGN | GGC | CCA | CNA | GNA | CAA | GAA | GAC | NCA | CGG | 576 |
| CGG | CNN | NGG | NNN | ANN | GNG | GGG | ANA | GNA | AGC | NGG | GGA | GAN | CAG | NGN | GGC | 624 |
| CNG | CCG | GAN | AAG | CCA | GGA | GNG | NAN | ACN | CGA | GNG | ACA | GCC | NAC | CNN | GAC | 672 |
| NGG | ANN | AGG | CAA | CAA | ACN | GGG | ANC |  |  |  |  |  |  |  |  | 696 |

(2) INFORMATION FOR SEQ ID NO:24:

(i) SEQUENCE CHARACTERISTICS:
        (A) LENGTH: 696 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:24:

|  |  |  |  |  |  |  |  |  |  |  |  |  |  |  |  |
|--|--|--|--|--|--|--|--|--|--|--|--|--|--|--|--|
| ATC | CTT | GGA | GGC | ACT | GAG | GCT | GAG | GAG | GGA | AGC | TGG | CCG | TGG | CAA | GTC | 48 |
| AGT | CTG | CGG | CTC | AAT | AAT | GCC | CAC | CAC | TGT | GGA | GGC | AGC | CTG | ATC | AAT | 96 |
| AAC | ATG | TGG | ATC | CTG | ACA | GCA | GCT | CAC | TGC | TTC | AGA | AGC | AAC | TCT | AAT | 144 |
| CCT | CGT | GAC | TGG | ATT | GCC | ACG | TCT | GGT | ATT | TCC | ACA | ACA | TTT | CCT | AAA | 192 |
| CTA | AGA | ATG | AGA | GTA | AGA | AAT | ATT | TTA | ATT | CAT | AAC | AAT | TAT | AAA | TCT | 240 |
| GCA | ACT | CAT | GAA | AAT | GAC | ATT | GCA | CTT | GTG | AGA | CTT | GAG | AAC | AGT | GTC | 288 |
| ACC | TTT | ACC | AAA | GAT | ATC | CAT | AGT | GTG | TGT | CTC | CCA | GCT | GCT | ACC | CAG | 336 |
| AAT | ATT | CCA | CCT | GGC | TCT | ACT | GCT | TAT | GTA | ACA | GGA | TGG | GGC | GCT | CAA | 384 |
| GAA | TAT | GCT | GGC | CAC | ACA | GTT | CCA | GAG | CTA | AGG | CAA | GGA | CAG | GTC | AGA | 432 |
| ATA | ATA | AGT | AAT | GAT | GTA | TGT | AAT | GCA | CCA | CAT | AGT | TAT | AAT | GGA | GCC | 480 |
| ATC | TTG | TCT | GGA | ATG | CTG | TGT | GCT | GGA | GTA | CCT | CAA | GGT | GGA | GTG | GAC | 528 |
| GCA | TGT | CAG | GGT | GAC | TCT | GGT | GGC | CCA | CTA | GTA | CAA | GAA | GAC | TCA | CGG | 576 |
| CGG | CTT | TGG | TTT | ATT | GTG | GGG | ATA | GTA | AGC | TGG | GGA | GAT | CAG | TGT | GGC | 624 |
| CTG | CCG | GAT | AAG | CCA | GGA | GTG | TAT | ACT | CGA | GTG | ACA | GCC | TAC | CTT | GAC | 672 |
| TGG | ATT | AGG | CAA | CAA | ACT | GGG | ATC |  |  |  |  |  |  |  |  | 696 |

(2) INFORMATION FOR SEQ ID NO:25:

(i) SEQUENCE CHARACTERISTICS:
        (A) LENGTH: 418 amino acids
        (B) TYPE: amino acid
        (C) STRANDEDNESS: single
        (D) TOPOLOGY: linear (xi) SEQUENCE DESCRIPTION: SEQ ID NO:25:

|  |  |  |  |  |  |  |  |  |  |  |  |  |  |
|--|--|--|--|--|--|--|--|--|--|--|--|--|--|
|  |  |  |  |  |  |  |  |  |  |  | Met | Tyr | Arg |
|  |  |  |  |  |  |  |  |  |  |  |  | -185 |  |
| Pro | Ala | Arg | Val | Thr | Ser | Thr | Ser | Arg | Phe | Leu | Asn | Pro | Tyr | Val | Val |
|  |  |  | -180 |  |  |  | -175 |  |  |  |  | -170 |  |  |  |

```
Cys Phe Ile Val Val Ala Gly Val Val Ile Leu Ala Val Thr Ile Ala
     -165                -160                -155

Leu Leu Val Tyr Phe Leu Ala Phe Asp Gln Lys Ser Tyr Phe Tyr Arg
     -150                -145                -140

Ser Ser Phe Gln Leu Leu Asn Val Glu Tyr Asn Ser Gln Leu Asn Ser
-135            -130                -125                    -120

Pro Ala Thr Gln Glu Tyr Arg Thr Leu Ser Gly Arg Ile Glu Ser Leu
             -115                -110                -105

Ile Thr Lys Thr Phe Lys Glu Ser Asn Leu Arg Asn Gln Phe Ile Arg
             -100             -95                     -90

Ala His Val Ala Lys Leu Arg Gln Asp Gly Ser Gly Val Arg Ala Asp
         -85             -80                     -75

Val Val Met Lys Phe Gln Phe Thr Arg Asn Asn Asn Gly Ala Ser Met
     -70             -65                     -60

Lys Ser Arg Ile Glu Ser Val Leu Arg Gln Met Leu Asn Asn Ser Gly
-55             -50                 -45                     -40

Asn Leu Glu Ile Asn Pro Ser Thr Glu Ile Thr Ser Leu Thr Asp Gln
             -35                 -30                      -25

Ala Ala Ala Asn Trp Leu Ile Asn Glu Cys Gly Ala Gly Pro Asp Leu
         -20                 -15                     -10

Ile Thr Leu Ser Glu Gln Arg Ile Leu Gly Gly Thr Glu Ala Glu Glu
         -5                   1                   5

Gly Ser Trp Pro Trp Gln Val Ser Leu Arg Leu Asn Asn Ala His His
10              15                  20                      25

Cys Gly Gly Ser Leu Ile Asn Asn Met Trp Ile Leu Thr Ala Ala His
             30                  35                      40

Cys Phe Arg Ser Asn Ser Asn Pro Arg Asp Trp Ile Ala Thr Ser Gly
             45                  50                  55

Ile Ser Thr Thr Phe Pro Lys Leu Arg Met Arg Val Arg Asn Ile Leu
             60                  65                  70

Ile His Asn Asn Tyr Lys Ser Ala Thr His Glu Asn Asp Ile Ala Leu
         75                  80                  85

Val Arg Leu Glu Asn Ser Val Thr Phe Thr Lys Asp Ile His Ser Val
90              95                  100                     105

Cys Leu Pro Ala Ala Thr Gln Asn Ile Pro Pro Gly Ser Thr Ala Tyr
             110                 115                     120

Val Thr Gly Trp Gly Ala Gln Glu Tyr Ala Gly His Thr Val Pro Glu
             125                 130                     135

Leu Arg Gln Gly Gln Val Arg Ile Ile Ser Asn Asp Val Cys Asn Ala
         140                 145                     150
```

-continued

| | | | | | | | | | | | | | | |
|---|---|---|---|---|---|---|---|---|---|---|---|---|---|---|
| Pro | His 155 | Ser | Tyr | Asn | Gly | Ala 160 | Ile | Leu | Ser | Gly | Met 165 | Leu | Cys | Ala | Gly |
| Val 170 | Pro | Gln | Gly | Gly | Val 175 | Asp | Ala | Cys | Gln | Gly 180 | Asp | Ser | Gly | Gly | Pro 185 |
| Leu | Val | Gln | Glu | Asp 190 | Ser | Arg | Arg | Leu | Trp 195 | Phe | Ile | Val | Gly | Ile 200 | Val |
| Ser | Trp | Gly | Asp 205 | Gln | Cys | Gly | Leu | Pro 210 | Asp | Lys | Pro | Gly | Val 215 | Tyr | Thr |
| Arg | Val | Thr 220 | Ala | Tyr | Leu | Asp | Trp 225 | Ile | Arg | Gln | Gln | Thr 230 | Gly | Ile | |

NUCLEIC ACID SEQUENCE ENCODING TRYPSIN-LIKE ENZYME AND PROCESS FOR PRODUCING THE ENZYME

BACKGROUND OF THE INVENTION

1. Field of the Invention

This invention relates to a DNA or RNA nucleic acid sequence encoding a trypsin-like enzyme, more detailedly a protease found in cough phlegm, etc. from patients suffering from chronic disease on the respiratory tract; and a process for producing the protease using the nucleic acid sequence.

2. Description of Related Art

It is known that various proteases exist in the human lungs and respiratory tract, and, for example as proteases derived from neutrophiles found in the lungs and respiratory tract of patients suffering from chronic disease on the respiratory apparatus, there are elastase, cathepsin G, collagenase, gelatinase, protease 3, etc. It is considered that neutrophiles act as a protection mechanism against foreign substances such as bacteria and viruses, but when inflammation grew worse or was made to be chronic, they cannot treat the foreign substances, and the release of the neutrophile proteases takes place by destruction of the neutrophiles themselves.

Further, it is also known that as to trypsin-like enzymes derived from mast cells, a tryptase having a molecular weight of about 140,000 exists in the lungs and respiratory tract, but its physiological role is not perfectly clarified (J.B.C., 259, 11046–11051, 1984).

As a trypsin-like enzyme different from this tryptase it is known a protease having a molecular weight of 20,000 crudely purified from cough phlegm of a patient suffering from chronic disease on the respiratory tract (The Japanese Journal of Thoracic Diseases, Vol. 30, Supplement, Apr./1992, p280, G-77, p319, I-36). It is shown that this protease digests a synthetic substrate for thrombin and a synthetic substrate for trypsin, and digests fibrinogen as a natural substrate, but its physiological role is unclear.

As to enzymes having an action of digesting fibrinogen which is a natural substrate, their application as an agent for treating various diseases is considered. Fibrin is contained in phlegm, particularly viscous phlegm in respiratory apparatus diseases such as bronchial asthma, and it is suggested that fibrin participates in the viscosity (The Japanese Journal of Thoracic Diseases, Vol. 31, Supplement, Mar./1993, p311, K1-58). Thus, a trypsin-like enzyme capable of selectively digesting fibrinogen which is a precursor of fibrin is expected to be utilized as an expectorant. Further, it is known that fibrin network formation participates in the implantation of tumor cells in the vascular floor during metastasis formation (Irish. J. Med. Sci. 394, 474–479, 1958), and further the fibrin network has a role of protecting tumor cells from immunocytes (Thromb. Diath. Haem. Sappl. 59, 139–156, 1974). Thus, a trypsin-like enzyme capable of digesting fibrinogen and decreasing fibrin network formation is expected to be used as a tumor cells implantation-inhibiting agent. Further, as to a trypsin-like enzyme capable of digesting fibrinogen in the blood vessel and prolonging blood coagulation time, its application as an anticoagulant in the broad sense to diseases in the circulatory system such as chronic arterial obstruction and peripheral circulatory disorder is expected.

SUMMARY OF THE INVENTION

The present inventors isolated an enzyme having trypsin activity (protease) from cough phlegm of a patient suffering from a chronic respiratory apparatus disease, determined the amino acid sequence composed of 20 amino acids at the N-terminus, synthesized a DNA encoding the above N-terminus amino acid sequence, succeeded in cloning a nucleic acid sequence encoding the enzyme according to rapid amplification of cDNA ends (hereafter, abbreviated as RACE) using this DNA, and determined the whole amino acid sequence of the enzyme.

Thus, the present invention provides a nucleic acid sequence encoding a trypsin-like enzyme having the following amino acid sequence [I](SEQ ID NO:19), or a biochemically equivalent of the enzyme.

| Ile | Leu | Gly | Gly | Thr | Glu | Ala | Glu | Gly | Gly | Ser | Trp | Pro |
| 1 | | | | 5 | | | | | 10 | | | |
| Trp | Gln | Val | Ser | Leu | Arg | Leu | Asn | Asn | Ala | His | His | Cys |
| | 15 | | | | | 20 | | | | | 25 | |
| Gly | Gly | Ser | Leu | Ile | Asn | Asn | Met | Trp | Ile | Leu | Thr | Ala |
| | | | 30 | | | | | 35 | | | | |
| Ala | His | Cys | Phe | Arg | Ser | Asn | Ser | Asn | Pro | Arg | Asp | Trp |
| 40 | | | | | 45 | | | | | 50 | | |
| Ile | Ala | Thr | Ser | Gly | Ile | Ser | Thr | Thr | Phe | Pro | Lys | Leu |
| | | 55 | | | | | 60 | | | | | 65 |
| Arg | Met | Arg | Val | Arg | Asn | Ile | Leu | His | Asn | Asn | Tyr | Lys |
| | | | | 70 | | | | 75 | | | | |
| Ser | Ala | Thr | His | Glu | Asn | Asp | Ile | Ala | Leu | Val | Arg | Leu |
| 80 | | | | | 85 | | | | | 90 | | |
| Glu | Asn | Ser | Val | Thr | Phe | Thr | Lys | Asp | Ile | His | Ser | Val |
| | | 95 | | | | | 100 | | | | | 105 |
| Cys | Leu | Pro | Ala | Ala | Thr | Gln | Asn | Ile | Pro | Pro | Gly | Ser |
| | | | | 110 | | | | | 115 | | | |
| Thr | Ala | Tyr | Val | Thr | Gly | Trp | Gly | Ala | Gln | Glu | Tyr | Ala |
| | 120 | | | | | 125 | | | | | 130 | |
| Gly | His | Thr | Val | Pro | Glu | Leu | Arg | Gln | Gly | Gln | Val | Arg |
| | | | 135 | | | | | 140 | | | | |
| Ile | Ile | Ser | Asn | Asp | Val | Cys | Asn | Ala | Pro | His | Ser | Tyr |
| 145 | | | | | 150 | | | | | 155 | | |
| Asn | Gly | Ala | Ile | Leu | Ser | Gly | Met | Leu | Cys | Ala | Gly | Val |
| | | 160 | | | | | 165 | | | | | 170 |
| Pro | Gln | Gly | Gly | Val | Asp | Ala | Cys | Gln | Gly | Asp | Ser | Gly |
| | | | | 175 | | | | | 180 | | | |
| Gly | Pro | Leu | Val | Gln | Glu | Asp | Ser | Arg | Arg | Leu | Trp | Phe |
| | 185 | | | | | 190 | | | | | 195 | |
| Ile | Val | Gly | Ile | Val | Ser | Trp | Gly | Asp | Gln | Cys | Gly | Leu |
| | | | 200 | | | | | 205 | | | | |
| Pro | Asp | Lys | Pro | Gly | Val | Tyr | Thr | Arg | Val | Thr | Ala | Tyr |
| 210 | | | | | 215 | | | | | 220 | | |
| Leu | Asp | Trp | Ile | Arg | Gln | Gln | Thr | Gly | Ile | | | |
| | | 225 | | | | | 230 | | | | | |

The trypsin-like enzyme which the nucleic acid sequence of the invention encodes is a protease existing in the human lower respiratory tract, particularly cough phlegm, respiratory tract mucus, respiratory tract washings, etc. of patients suffering from chronic diseases on the respiratory tract, and has physicochemical characteristics as stated below.

① Action: Trypsin-like protease (proteolytic enzyme) activity.

② Substrate specificity: The enzyme digests well a synthetic substrate for trypsin and a synthetic substrate for thrombin, but does not digest a synthetic substrate for chymotrypsin, a synthetic substrate for elastase, a synthetic substrate for collagenase, and a synthetic substrate for leucine aminopeptidase.

③ Optimum pH: 8.2–9.2 (Tris-HCl buffer), particularly around 8.6 in activity assay using the synthetic substrate for trypsin.

④ Titer assay method: Assay of protease activity using the synthetic substrate for trypsin.

⑤ Temperature for action: About 37° C.

⑥ Inactivation by pH: At pH 6.0, about 80% of the enzyme at pH 7.6 is inactivated.

⑦ Inhibition: Inhibited by DFP (diisopropyl fluorophosphate), PMSF (phenylmethylsulfonyl fluoride) (the above two are serine protease inhibitors), leupeptin and antipain (the above two are trypsin inhibitors).

⑧ Purification method: Purified from cough phlegm of a patient suffering from chronic disease on the respiratory apparatus by column chromatography.

⑨ Molecular weight: 28,000 Da [by the SDS-polyacrylamide gel electrophoresis method (hereafter, referred to as SDS-PAGE)].

More detailedly, the above trypsin-like enzyme well digests
  a synthetic substrate for trypsin:
  Boc-Phe-Ser-Arg-MCA and
  Boc-Gln-Ala-Arg-MCA, and
  a synthetic substrate for thrombin:
  Boc-Val-Pro-Arg-MCA,
slightly digests
  a synthetic substrate for factor Xa:
  Boc-Ile-Gln-Gly-Arg-MCA (SEQ ID NO:20),
  a synthetic substrate for urokinase:
  Boc-Gln-Gly-Arg-MCA, and
  a synthetic substrate for plasmin:
  Boc-Val-Leu-Lys-MCA,
and does not digest
  a synthetic substrate for chymotrypsin:
  Suc-Ala-Ala-Pro-Phe-MCA (SEQ ID NO:21),
  a synthetic substrate for elastase:
  Suc-Ala-Pro-Ala-MCA, and
  a synthetic substrate for collagenase:
  Suc-Gly-Pro-Leu-Gly-Pro-MCA (SEQ ID NO:22)
(herein, MCA means methylcoumarinamide).

Further, as to natural substrates, the trypsin-like enzyme digests fibrinogen, VIP (vasoactive intestinal peptide), but does not digest IgA, IgG, albumin, α1-antitrypsin and substance P.

Further, in contrast to trypsin, the trypsin-like enzyme also has an action of inactivating influenza viruses, NDV Miyadera strain and VSV New Jersey strain (see: The Society of Japanese Virologist, the 42th General Meeting Lecture Extracts, p201, No. 4022).

The trypsin-like enzyme having physicochemical characteristics as stated above can be obtained by isolating and purifying it from, for example, cough phlegm, respiratory tract mucus, respiratory tract washings, etc. of patients suffering from chronic disease on the respiratory tract, according to the method specifically described in the later-described Example 1, for example, by chromatography using one of or a combination of two or more of hydrophobic chromatography, ion exchange chromatography, reverse-phase chromatography, affinity chromatography, gel filtration chromatography, etc.

The "biochemically equivalent" of the trypsin-like enzyme in the invention, means a polypeptide wherein one or plural amino acids in the amino acid sequence of the trypsin-like enzyme are deleted, one or plural amino acids are added at the terminus or in the strand of the amino acid sequence, and/or one or plural amino acids in the amino acid sequence are replaced by other amino acids, the polypeptide holding substantially equivalent biochemical characteristics to those of the trypsin-like enzyme. As examples of such biochemical equivalents, there can be mentioned one having a similar enzymatic activity, one recognizable with same antibodies, etc.

The nucleic acid sequence of the invention encoding the trypsin-like enzyme or a biochemical equivalent thereof can be synthesized according to the RACE method (Frohman, M. A. et al. Proc. Natl. Acad. Sci. USA, 85, 8998–9002 (1988)), and the outline of the method is described as follows.

In general, the RACE method is a method for efficiently obtaining, when part of the sequence of a cDNA is known, the full length cDNA based thereon. Namely, it is a method of obtaining the cDNA by amplifying the fragment between the 3'-terminus or 5'-terminus of the mRNA and the known sequence at the middle thereof using PCR. A primer is prepared in such a manner that a strand can be extended in the direction of the 3'-terminus or 5'-terminus from this known sequence region, and then the cDNA is synthesized. Thus, in PCR are used a primer which specifically anneals to the known region, and a primer which anneals, at the 3'-terminus, to the poly (A) sequence of the mRNA, whereas a primer which anneals, at the 5'-terminus, to a sequence added by tailing reaction or ligation reaction or the like. Then, utilizing the parts of the duplicated sequences, the synthesized cDNA sequence of the 3'-terminus side and synthesized cDNA sequence of the 5'-terminus side are ligated to give the full length cDNA.

More specifically, the N-terminus amino acid sequence 20 residues of a trypsin-like enzyme isolated from cough phlegm of a patient suffering from human chronic disease on the respiratory tract is sequenced, and, based on this sequence, an oligonucleotide mixture capable of encoding the 1st to 7th amino acids, and an oligonucleotide mixture of the complementary strand of a sequence capable of encoding the 15th to 20th amino acids are produced taking the degeneracy of the corresponding codons. When PCR is conducted using them as primers (degenerate primers) and the human trachea cDNA as a template, a 59 bp DNA fragment is preferentially amplified. By sequencing this 59 bp fragment according to a usual method, it is revealed that this 59 bp DNA fragment is part of the cDNA of the trypsin-like enzyme because it encodes the N-terminus amino acid sequence 19 residues of the trypsin-like enzyme. Based on the sequence of this part of the cDNA, the sequence of the full length cDNA can be obtained according to such a manner as described below.

First, it is described how to obtain the cDNA of the 3'-terminus side. A single-strand cDNA is synthesized from a human trachea mRNA with a reverse transcriptase using an oligo dT primer having an additional sequence ① at the 5'-terminus side. PCR is conducted with this single-strand cDNA as a template, using a primer specifically annealing to part of the above 59 bp fragment sequence and a primer corresponding to the additional sequence ①. By repeating PCR using the same primers or primers located in the inner positions, in accordance with the degree of amplification, an amplified product can be obtained, the cDNA of the 3'-terminus side is cloned using this amplified product, and sequencing can be made.

As to the 5'-terminus side, a single-strand cDNA is synthesized from the human trachea mRNA using a primer specifically annealing to the determined cDNA sequence. This single-strand cDNA is purified, and an additional sequence ② is ligated to the 3'-terminus through ligation reaction. Using this as a template, PCR is conducted with a primer specifically annealing to a sequence located in an inner position than the primer used in the reverse transcription, and a primer corresponding to the additional sequence ②. Thereafter, the same operations as in the 3'-terminus side can be conducted to conduct sequencing.

Utilizing the parts of the duplicated sequences, the cDNAs of the 3'-terminus side and the 5'-terminus side can be ligated to give the full length cDNA of the trypsin-like enzyme.

The trypsin-like enzyme gene cDNA sequence thus synthesized and cloned has a base sequence shown in Sequence No. 15, and this sequence can be integrated as it is into a vector plasmid, an appropriate host can be transformed with the plasmid, and the gene can be expressed. Further, it is also possible to synthesize the corresponding mRNA sequence using the cDNA as a template.

Thus, the nucleic acid sequence of the invention can, specifically, have the following sequence [II] (SEQ ID NO:23).

AXC CXX GGA GGC ACX GAG GCX GAG GAG GGA AGC XGG CCG XGG CAA GXC

AGX CXG CGG CXC AAX AAX GCC CAC CAC XGX GGA GGC AGC CXG AXC AAX

AAC AXG XGG AXC CXG AXA GCA GCX CAC XGC XXC AGA AGC AAC XCX AAX

CCX CGX GAC XGG AXX GCC ACG XCX GGX AXX XCC ACA ACA XXX CCX AAA

CXA AGA AXG AGA GXA AGA AAX AXX XXA AXX CAX AAC AAX XAX AAA XCX

GCA ACX CAX GAA AAX GAC AXX GCA CXX GXG AGA CXX GAG AAC AGX GXC
ACC XXX ACC AAA GAX AXC CAX AGX GXG XGX CXC CCA GCX GCX ACC CAG
AAX AXX CCA CCX GGX XCX ACX GCX XAX GXA AXA GGA XGG GGC GCX CAA
GAA XAX GCX GGC CAC ACA GXX CCA GAG CXA AGG CAA GGA CAG GXC AGA
AXA AXA AGX AAX GAX GXA XGX AAX GCA CCA CAX AGX XAX AAX GGA GCC
AXC XXG XCX GGA AXG XCG XGX GCX GGA GXA CCX CAA GGX GGA GXG GAX
GCA XGX CAG GGX GAC XCX GGX GGX CCA CXA GXA CAA GAA GAC XCA CGG
CGG CXX XGG XXX AXX GXG GGG AXA GXA AGC XGG GGA GAX CAG XGX GGC
CXG CCG GAX AAG CCA GGA GXG XAX ACX CGA GXG ACA GCC XAC CXX GAC
XGG AXX AGG CAA CAA ACX GGG AXC wherein X represents T or U.

Further, the coding strand encoding the trypsin-like enzyme not only can exist in the form of the above continuous base sequence (cDNA or mRNA), but can exist, as a gene of exon-intron structure which is a precursor of the cDNA or mRNA, in such an intermittent form that the coding strand is discontinued by intervention of introns.

It is possible, by using the nucleic acid sequence of the invention, to produce the trypsin-like enzyme having the above amino acid sequence or a biochemical equivalent thereof.

Although a trypsin-like enzyme can be purified from human cough phlegm, this method is complicated and expensive because the availability of the starting material is limited and the concentration of the trypsin-like enzyme is low. Production of a trypsin-like enzyme in a useful amount is apparently important (in view of possibility of clinical application of the trypsin-like enzyme).

A process for producing a trypsin-like enzyme or a biochemical equivalent thereof according to genetic engineering is described below.

The trypsin-like enzyme or a biochemical equivalent thereof (hereafter, sometimes generically referred to as trypsin-like enzyme, for convenience) according to the invention can, for example, be produced by growing a host cell transformed or infected with a vector or virus containing a sequence which contains (a) a promoter:

(b) optionally, an enhancer stimulating the promoter; and (c) the following DNA sequence [III] whose transcription can be initiated by promoter (A)m-(B)n-C [III]

wherein

A represents a DNA sequence encoding a signal peptide (prepeptide) and/or a prepropeptide, B represents a DNA sequence encoding a cleavage sequence or a translation initiation codon, m represents 0 or 1, and n represents 0 or 1, and C represents a DNA sequence encoding the amino acid sequence of the above formula [I], and wherein these (a), (b) and (c) are arranged so that a trypsin-like enzyme may be expressed, and isolating the trypsin-like enzyme secreted or accumulated.

In the above sequence [III], the sequence A is a DNA sequence encoding a signal peptide (prepeptide) and/or a prepropeptide, and these signal peptide (prepeptide) and/or prepropeptide can be peptides functioning as a signal peptide (prepeptide) and/or a prepropeptide in a host cell wherein the desired protein is expressed.

Further, in the above sequence [III], the sequence B is a DNA sequence encoding a cleavage sequence or a translation initiation codon, and as a sequence usable for such purpose is desirable a sequence cleavable with a signal peptidase or processing protease of the host cell, an enzymatically cleavable sequence, or Met. The amino acid of this cleavage sequence is an amino acid corresponding to the kinds of the signal peptide (prepeptide) and/or a prepropeptide, as stated above. As the amino acid of the cleavage sequence, there can, for example, be mentioned Gln, Ala, Ser, Glu, Arg, Lys, Asp, Gly, etc., and as a DNA sequence encoding the sequence, there can, for example, be mentioned CAG corresponding to Gln. Further, as a DNA sequence encoding the sequence of Met which is the amino acid of the translation initiation codon, ATG can be mentioned.

The sequence C represents the DNA sequence of the trypsin-like enzyme or a protein biochemically equivalent thereto. For example, in such a range that substantially the same function as the DNA sequence of the trypsin-like enzyme has is maintained, part of the DNA can be changed by replacement, insertion or deletion. Herein, the protein biochemically equivalent to the trypsin-like enzyme includes a protein detectable by an immunochemical assay method for the trypsin-like enzyme, more preferably one detectable by an enzymological assay method therefor.

As such sequence C, a DNA sequence encoding the aforesaid amino acid sequence [I] of the mature trypsin-like enzyme can be mentioned, but, for convenience, a human cDNA represented by the aforesaid base sequence [II] herein X represents T can be used.

The DNA compound of the invention encoding a trypsin-like enzyme is particularly suitable for transforming or infecting an insect cell or another eucaryotic host cell therewith, and expressing a trypsin-like enzyme activity. Many insect and mammal host cells have a cellular mechanism necessary for recognizing the signal peptide (prepeptide) and/or prepropeptide existing at the N-terminus of the trypsin-like enzyme, and conducting appropriate processing. There are extensive and various vectors or viruses for transformation or infection of eucaryotic host cells, and any limitation of the scope of the invention is not intended at all by specific vectors or viruses exemplified below.

As to means for expressing a desired protein in a eucaryotic cell, a lot of systems are well-known in the concerned field.

For example, as a system for expression in a yeast, there can be mentioned "Expression of Polypeptide in Yeast" disclosed in Japanese Laid-open Patent Publication No. 159489/1982 (=EP 60057 B), and as a system for expression in an insect cell, there can be mentioned "Process for Producing Recombinant Baculovirus Expression Vector" disclosed in Japanese Laid-open Patent Publication No. 37988/1985 (=U.S. Pat. Nos. 4,745,051 and 4,879,236), and as a system for expression in a mammalian cell, there can be mentioned "Improvement of Eucaryotic Expression" disclosed in Japanese Laid-open Patent Publication No. 171198/1990 (=EP 363127A$_3$), but there are many other systems than these.

A process for producing a trypsin-like enzyme in a eucaryotic host cell is described below taking a case of using, as a representative example, a baculovirus expression system exemplified above. In this case, a promoter which the baculovirus has is used as the eucaryotic promoter. A promoter which a virus with which a eucaryotic cell is infected has is a "eucaryotic promoter" because it expresses its promoter function in a eucaryotic cell.

Further, an enhancer disposed so as to stimulate it can, optionally, be easily disposed by utilizing an enhancer of the baculovirus. The most convenient means for these constitution can be accomplished by utilizing a protein expression system, for example, a polyhedrin gene which a baculovirus has, and conducting the substitution or insertion of a DNA sequence encoding the above amino acid sequence [I], more preferably a DNA sequence represented by the above formula [III] at the polyhedrin gene region.

More specifically, a desired protein can, for example, be produced by using the full EcoRI-I fragment [R. D. Posse et al., Virology, 185 (1991), 229–241] of Autographa californica multiple nuclear polyhedrosis virus: AcMNPV, conducting the substitution or insertion of the above DNA sequence at its polyhedrin gene part to prepare a mutant virus, infecting an insect cell, for example an established strain SF-9 (ATCC CRL1711) of the *Spodoptera frugiperda* with the virus, and culturing the infected cell. The above preparation of a mutant virus can, for convenience, be conducted by homologous recombination, and a specific means therefor is also detailedly described in Japanese Laid-open Patent Publication No. 37988/1985. For preparation of the above expression system, the baculovirus AcMNPV, a vector for homologous recombination and the SF-9 strain are necessary as starting materials. Such an expression system is sold from Funakoshi Co., Ltd. (MaxBac$^R$ Baculovirus Expression system; INV IV-0822-04), and anyone can obtain it. Further, as to baculoviruses themselves, one can obtain one from nature according to the method described in G. E. Smith & M. D. Summers, Virology, 89 (1978), 517–527.

Further, a vector for homologous recombination an also be obtained, for example by inserting the above EcoRI-I fragment of AcMNPV in the EcoRI site of pBR322, and replacing the part of the polyhedrin structural gene by the DNA sequence represented by the formula [III].

The thus obtained vector for homologous recomination can be mixed with the baculovirus AcMNPV, and then the SF-9 culture cell can be cotransfected with the mixture. A virus population comprising recombinant baculoviruses and non-recombinant baculoviruses is obtained by such operations. Usually, $10^5$ to $10^6$ pfu/ml of viruses exist in the supernatant of the third day from the transfection. When dilution is conducted so that 100 plaques may be formed per 35 ml-dish, assay is conducted, ½ to ⅓ of the mixtures become colorless, transparent plaques, or when the vector for homologous recombination has a lacZ marker gene, become blue-stained plaques with X-gel in each medium. These are selected as candidate strains as a recombinant baculovirus, and the viruses are recovered. Among these candidate strains, a recombinant baculovirus can be obtained by detecting a DNA encoding a trypsin-like enzyme according to the PCR method or a hybridization method. A large amount of this recombinant baculovirus can be produced by taking a method of infecting fresh SF-9 cells again with the recombinant baculovirus.

In the above method, non-infected SF-9 cells can be cultured at 28° C. in a medium containing 10% bovine serum.

SF-9 culture cells which are being cultured and maintained in a medium are infected with the above recombinant baculovirus, and made to express the protein. This can be attained by continuing culture at 28° C. for time of the order of 72 to 96 hours in the above medium or a serum-free medium.

The resultant culture broth contains the desired protein, AcMNPV, SF-9 cells, SF-9 dead cells, and DNAs and proteins derived from SF-9 or AcMNPV. Therefore, for obtaining the trypsin-like enzyme, the trypsin-like enzyme is purified and separated from the culture broth according to the following operations.

Purification process from culture supernatant
(1) Cells are centrifuged.
(2) The virus is removed by ultrafiltration.
(3) Dialysis or dilution is conducted against or with 50 mM Tris hydrochloric acid—500 mM sodium chloride buffer (pH 8.0).

(4) The resultant sample is loaded on a benzamidine affinity column equilibrated with 50 mM Tris hydrochloric acid—500 mM sodium chloride buffer (pH 8.0), washed with the same buffer, and eluted with 10 mM hydrochloric acid—500 mM sodium chloride solution (pH 2.0), and detection is conducted on trypsin-like enzyme activity, and the main peak is collected.

The resultant trypsin-like enzyme exhibits one band by SDS-PAGE.

Purification process from cultured cells (1) The cells are centrifuged and collected.

(2) The cells are suspended in 50 mM Tris hydrochloric acid—500 mM sodium chloride buffer (pH 8.0).

(3) Triton X-100 is added so that its final concentration becomes 1%, and the mixture is allowed to stand at 0° C. for 60 minutes to dissolve the cells.

(4) The cell debris is centrifuged.

(5) The supernatant is dialized against or diluted with 50 mM Tris hydrochloric acid—500 mM sodium chloride buffer (pH 8.0).

(6) The resultant sample is loaded on a benzamidine affinity column equilibrated with 50 mM Tris hydrochloric acid—500 mM sodium chloride buffer (pH 8.0), washed with the same buffer, and eluted with 10 mM hydrochloric acid—500 mM sodium chloride solution (pH 2.0), and detection is conducted on trypsin-like enzyme activity, and the main peak is collected.

The resultant trypsin-like enzyme exhibits one and by SDS-PAGE.

The DNA compound of the invention can also be expressed in procaryotic host cells such as, *Escherichia coli, Bacillus subtilis* and Streptomyces. By expressing a DNA encoding a trypsin-like enzyme activity in a procaryotic host cell, the trypsin-like enzyme can be produced. The trypsin-like enzyme can be used as an antigen for stimulating production of trypsin-like enzyme-specific antibodies, or also for quantitative analysis of a trypsin-like enzyme. In many assay methods, for assaying the level of a protein in a sample, competitive antibody binding is utilized. Namely, a procaryote-produced trypsin-like enzyme labeled with radioactivity (or by another method) can be used as a "competing molecule" in assay of a trypsin-like enzyme in the respiratory tract humor.

Usually, procaryotes do not effectively make processing on eucaryotic signal peptides (prepeptides) and/or prepropeptides. Therefore, it is, somewhat, inefficient to express the part encoding the signal peptide (prepeptide) and/or prepropeptide of the trypsin-like enzyme structural gene, in a procaryote. Thus, it is also possible, before expressing a DNA compound encoding the trypsin-like enzyme activity, in a procaryotic host cell, to remove the DNA encoding the prepropeptide. Further, although not particularly illustrated in the present specification, the invention also includes a fusion between the coding DNA of a procaryotic signal peptide (prepeptide) and the coding DNA of a trypsin-like enzyme activity, aiming to express and secrete the trypsin-like enzyme in a procaryote.

The -186th to -1st amino acid residues (see Sequence No. 15) of the nascent polypeptide of the trypsin-like enzyme are surmised to encode a signal peptide (prepeptide) for extracellular secretion and a propeptide, and do not exist in a mature trypsin-like enzyme. It is not necessary that these regions of the trypsin-like enzyme are encoded in a procaryotic expression vector, but in the invention, a procaryotic expression vector encoding the prepropeptide of the trypsin-like enzyme can also be used.

Since selection of a promoter is not a critical thing for the feasibility of the invention, expression of the trypsin-like enzyme in *Escherichia coli* is never limited to use of a specific promoter. There can be mentioned, as examples, promoters of *Escherichia coli* lactose (lac), *Escherichia coli* trp, bacteriophage $\lambda P_L O_L$, bacteriophage $\lambda P_R O_R$, etc., but promoters therefore are not limited thereto. Further, it is also possible to conduct the expression of the trypsin-like enzyme structural gene, using one or more promoters, for example, the trp promoter and the lac promoter, disposed in series, or using a hybrid promoter such as the tac promoter. All the above promoters are already characterized, well-known by a person skilled in the art, and can be assembled synthetically or from a known plasmid.

When a foreign gene such as the trypsin-like enzyme of the invention is cloned downstream of the lac promoter, the synthetic rate of the protein remarkably increases due to induction by lactose, and at the same time proteinic granules are formed in the cells. The homogeneity of the protein composition of these granules is high, and at least 50%, mostly 80% (these are dry weight %) or more of these granules are composed of the desired protein product. These granules can easily be isolated from the cell lysate, and are stable if washed with urea of a low concentration or a detergent solution. By the washing, proteins nonspecifically binding to the granules are removed.

The procaryotic expression vector can be applied to various host organisms, above all, Gram-negative bacteria such as *Escherichia coli, Escherichia coli* K12, *Escherichia coli* K12 C600, *Escherichia coli* K12 HB101, and *Escherichia coli* K12 JM109.

The present invention is not limited to use of the actual selective markers contained in the recombinant plasmids or viruses exemplified in the present specification. There exist extensive and various selective markers, of eucaryotic and procaryotic host cells, suitable for being used in recombinant DNA vectors or viruses containing the DNA compound (or sequence) of the invention.

Many modifications and changes can be made on the exemplified DNA sequences, plasmids and viruses of the invention. For example, because of the degeneracy of genetic codes, replacement of nucleotides can be conducted, through the whole coding region of the polypeptide. Such sequences can be surmised from the amino acid sequence or DNA sequence of the trypsin-like enzyme, and can be assembled according to the following usual synthetic methods. Such synthesis can, substantially, be conducted according to the method of Itakura et al. (Itakura et al., 1977, Science, 198: 1059) and the method of Crea et al. (Crea et al., 1978, Proceedings of the National Academy of Sciences USA 75: 5765). Therefore, the invention is not limited to the DNA sequence, plasmids and viruses particularly exemplified.

As will be understood by a person skilled in the art, expression vectors or viruses in the invention can be used in any of eucaryotic and procaryotic host cells, and thereby, a polypeptide having the trypsin-like enzyme activity can be expressed in the host.

In the case of a vector containing a promoter which functions in the host cell and starts the transcription of the trypsin-like enzyme structural gene, when the host cell is transformed or infected therewith, if the host cell has a cellular mechanism for conducting the processing of the signal peptide (prepeptide) and/or prepropeptide, the trypsin-like enzyme can be isolated from the medium. Under another expression situation, if the host cell does not have a cellular mechanism for conducting the processing of the signal peptide (prepeptide) and/or prepropeptide, the trypsin-like enzyme must be isolated from the host cell.

The invention is further specifically described below according to examples, but it should be understood that these examples are not ones for restricting the scope of the invention.

Explanation on reagents and experimental operations (1) Unless otherwise particularly stated, DNA modification enzymes (e.g., ampliTaq DNA polymerase) and kits obtained from Takara, Pharmacia, Boehringer.Mannheim and CLONTECH are used following the instructions of the makers.

(2) An oligonucleotide can be synthesized by Applied Biosystems Model 394 DNA/RNA Synthesizer, and purified by OPC (Oligonucleotide Purification Cartridge) columns produced by the same company.

(3) PCR (Polymerase Chain Reaction) can be conducted by DNA Thermal Cycler produced by Perkin-Elmer Cetus Instruments Co. using the ampliTaq DNA polymerase, thereby specifically amplifying DNAs.

(4) An Escherichia coli cell can be transformed according to the method described in Maniatis et al., Molecular Cloning: A Laboratory Manual, Cold Spring Harbor Laboratory, 1982.

(5) A plasmid can be prepared by culturing an *E. coli* carrying plasmid at 37° C. overnight on about 25 cm$^2$ of L broth agar medium (1% peptone, 1% NaCl, 0.5% yeast extract and 1.5% agar), and then using QIAGEN Plasmid Kit produced by QIAGEN Co.

DETAILED DESCRIPTION OF THE PREFERRED EMBODIMENT(S)

EXAMPLE 1

Figure 1:
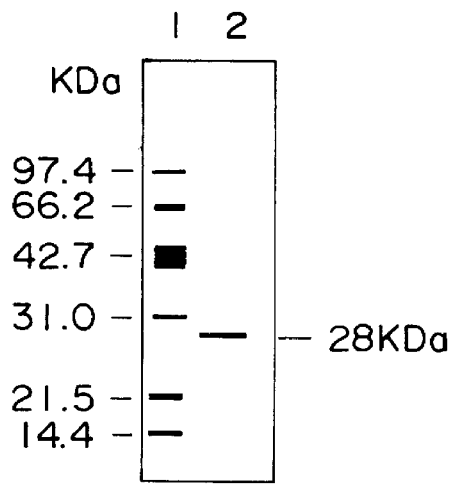
FIG. 1 is an SDS-PAGE pattern used for measurement of the molecular weight of the trypsin-like enzyme obtained in Example 1.

Isolation and purification of trypsin-like enzyme 1,000 ml of cough phlegm itself from a patient suffering from a chronic respiratory apparatus disease was mixed with the same amount of 0.05M Tris-HCl buffer (pH 7.5), 0.3M NaCl, and the mixture was homogenized for 1 minute under ice cooling by a homogenizer, and centrifuged (19,000 rpm). Ammonium sulfate was added to the supernatant so that the final concentration could be 40%. The precipitate was removed by centrifugation (10,000 rpm), proteases in the supernatant were adsorbed on Butyl Toyoperl Gel, and protease fractions were eluted using 5% (NH$_4$)$_2$SO$_4$; 10% glycerol; 0.05M Tris-HCl (pH 7.5).

Ammonium sulfate was added to the eluate so that the final concentration could be 65%, the mixture was centrifuged (10,000 rpm), the resultant precipitate was dissolved in 0.05 M acetate buffer (pH 4.0), 10% glycerol to make the whole volume 100 ml, and the solution was dialyzed against the same buffer. Proteases in the dialyzed solution were adsorbed on SP-Toyoperl 650M Gel, washed three times with 0.05M acetate buffer (pH 4.0) and twice 0.05M acetate buffer (pH 4.0), 0.1M NaCl, and protease fractions were eluted with 0.05M acetate buffer (pH 4.0), 10% glycerol, 0.3M NaCl. Ammonium sulfate was added to the eluate so that the final concentration could be 80%, the mixture was centrifuged (8,000 rpm), the resultant precipitate was dissolved in 40 ml of 0.05M acetate buffer (pH 4.0), 10% glycerol, and the solution was dialyzed against the same buffer.

The dialyzed solution was again poured on SP-Toyoperl 650 column (1.2×2 cm), and subjected to gradient elution of from 0.05M acetate buffer (pH 4.0), 10% glycerol to 0.05M acetate buffer (pH 4.5), 10% glycerol, 0.2M NaCl to give protease fractions. The eluate was concentrated to about 30 ml by ultrafiltration (YM10 membrane), and the concentrate was dialyzed against 0.05M Tris-HCl (pH 9.2), 10% glycerol, 0.5M NaCl.

The dialyzed solution was purified by affinity chromatography. Namely, the dialyzed solution was poured on a benzamidine-Sepharose 6B column, washed with 0.05M Tris-HCl (pH 9.2), 10% glycerol, 0.5M NaCl, and eluted with 0.05M acetate buffer (pH 4.0), 10% glycerol, 0.5M NaCl to give a solution of a purified protein. This trypsin-like enzyme was analyzed by SDS-polyacrylamide gel electrophoresis, and as a result, it was detected as a single band at a molecular weight of 28,000 (FIG. 1).

As molecular-weight markers, the following ones available from Bio-Rad Laboratories were used.

97. 4 kDa: Phosphorylase b
66. 2 kDa: Albumin
42. 7 kDa: Ovalbumin
31. 0 kDa: Carbonic anhydrase
21. 5 kDa: Soybean trypsin inhibitor
14. 4 kDa: Lysozyme

EXAMPLE 2

Assay method of trypsin activity

50 μl of the solution of the trypsin-like protease obtained in Example 1 was added to 1.5 ml of 0.1M Tris-HCl buffer (pH 8.6) containing 100 μM of a synthetic substrate for trypsin Boc-Phe-Ser-Arg-MCA (MCA=methylcoumarinamide), and the mixture was subjected to incubation at 37° C. for 1 hour. 1 ml of 30% acetic acid was then added, the amount of 7-amino-4-methylcoumarin (AMC) formed was determined by fluorescent assay (fluorescence 440 nm, excitating light 380 nm), and the activity of the enzyme was calculated based thereon. An activity of forming 1 pM of AMC in 1 minute is defined as 1 unit (1 unit=1 pM AMC/min).

EXAMPLE 3

Measurement of optimum pH of trypsin-like enzyme

The following buffers were prepared for ascertaining trypsin activity at various pH values.

EMES buffers;
pH 6.0, 6.2, 6.4, 6.6, 6.8
HEPES buffers;
pH 6.8, 7.0, 7.2, 7.4, 7.6
Tris buffers;
pH 7.4, 7.6, 7.8, 8.0, 8.2, 8.4, 8.6, 8.7, 8.8, 9.0, 9.2, 9.4

Figure 2:
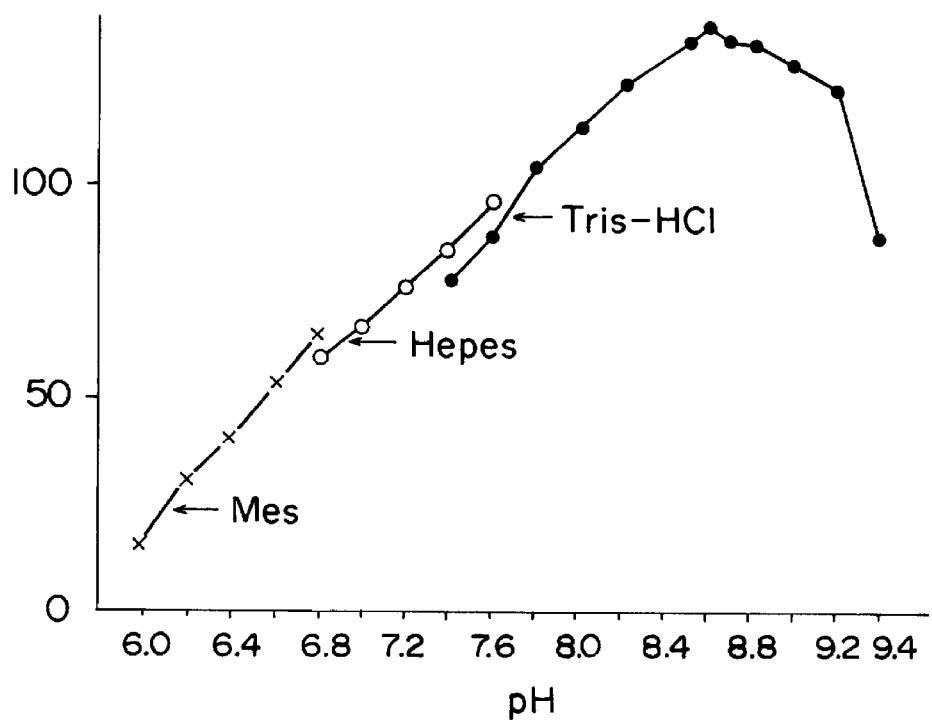
FIG. 2 is a graph showing the influence of pH on the activity of the trypsin-like enzyme obtained in Example 1.

The activity of the trypsin-like enzyme obtained in Example 1 in each buffer was assayed according to the method described in Example 2, and the results are shown in FIG. 2.

The enzyme exhibited strong activity in the range of pH 8.2 to 9.2, and, above all, the highest activities were exhibited at pH 8.4, 8.6, 8.7 and 8.8.

EXAMPLE 4

Substrate specificity of trypsin-like enzyme (1) Synthetic substrate

The activity of the trypsin-like enzyme obtained in Example 1 was assayed according to the method described in Example 2, using as a reaction buffer 0.1M Tris-HCl buffer (pH 8.6), and using a substrate for trypsin (Boc-Phe-Ser-Arg-MCA, Boc-Gln-Ala-Arg-MCA), a substrate for thrombin (Boc-Val-Pro-Arg-MCA), a substrate for factor Xa (Boc-Ile-Gln-Gly-Arg-MCA), a substrate for urokinase (Boc-Gln-Gly-Arg-MCA), a substrate for plasmin (Boc-Val-Leu-Lys-MCA), a substrate for chymotrypsin (Boc-Ala-Ala-Pro-Phe-MCA), a substrate for elastase (Suc-Ala-Pro-Ala-MCA), a substrate for collagenase (Suc-Gly-Pro-Leu-Gly-Pro-MCA) and a substrate for leucine aminopeptidase (Leu-MCA). The reactivity of the trypsin-like enzyme on each substrate in the case where the activity thereof on Boc-Phe-Ser-Arg-MCA (a substrate for trypsin) was taken to be 100% was shown in Table 1. Further, also as to a human neutrophile elastase and a rat mast cell-derived tryptase, the reactivities of the enzymes on each substrate in the case where the activities thereof on Suc-Ala-Pro-Ala-MCA and Suc-Phe-Ser-Arg-MCA were taken to be 100%, respectively, were shown in Table 1.

EXAMPLE 5

Effect of protease inhibitors on trypsin-like enzyme

As protease inhibitors were used serine protease inhibitors DFP (diisopropyl fluorophosphate) and PMSF (phenylmethylsulfonyl fluoride, trypsin inhibitors leupeptin and antipain, an elastin inhibitor elastinol, a leucine aminopeptidase inhibitor bestatin, a chymotrypsin inhibitor amastatin, and a blood protease inhibitor α1-antitrypsin, and the inhibition effect of these protease inhibitors on the trypsin-like enzyme obtained in Example 1, a human-derived neutrophile elastase and a rat mast cell-derived tryptase was assayed. As to the concentration of the inhibitors, only that of PMSF was made to be 1 mM and those of the other inhibitors were made to be 10 μM. After each inhibitor and the enzyme were reacted, enzymatic activity was assayed according to the method described in Example 2, and the inhibition ratio (%) of the enzymatic activity by the inhibitor was calculated and shown in Table 2.

As a result, the trypsin-like enzyme was inhibited by DFP, PMSF, leupeptin, antipain and α1-antitrypsin, but not inhibited by elastinol, bestatin and amastatin. Judging from the substrate specificity and the inhibition effect of each inhibitor, the trypsin-like enzyme exhibited properties different from those of the human neutrophile elastase and the rat mast cell-derived tryptase.

TABLE 1

Substrate specificity of trypsin-like enzyme

| | | Substrate digestion ratio (%) | | |
|---|---|---|---|---|
| Substrate | | Trypsin-like | Neutrophile | Rat mast cell |
| Synthetic substrate | Enzyme corresponding to substrate | enzyme pH 8.6 | elastase pH 8.6 | Tryptase pH 8.6 |
| Boc-Phe-Ser-Arg-MCA | Trypsin | 100 | 0.4 | 100 |
| Boc-Gln-Ala-Arg-MCA | Trypsin | 52.2 | 0.3 | — |
| Boc-Val-Pro-Arg-MCA | Thrombin | 74.6 | 0.2 | 50.6 |
| Boc-Ile-Gln-Gly-Arg-MCA | factor Xa | 13.1 | 0.3 | 149.0 |
| Boc-Gln-Gly-Arg-MCA | Urokinase | 13.8 | 0.2 | 4.6 |
| Boc-Val-Leu-Lys-MCA | Plasmin | 3.9 | 0.1 | 6.1 |
| Suc-Ala-Ala-Pro-Phe-MCA | Chymotrypsin | 0 | 0.1 | 2.0 |
| Suc-Ala-Pro-Ala-MCA | Elastase | 0 | 100 | — |
| Suc-Gly-Pro-Leu-Gly-Pro-MCA | Collagenase | 0 | 0 | — |
| Leu-MCA | Leucine aminopeptidase | 0 | 0.2 | — |

As a result, the trypsin-like enzyme obtained in Example 1 well digested the substrate for trypsin and the substrate for thrombin, and did not exhibit chymotrypsin activity, elastase activity, collagenase activity nor leucine aminopeptidase activity. The human neutrophile elastase and the rat mast cell-derived tryptase differed in point of substrate specificity.

(2) Natural substrates

IgA, IgG, albumin, α1-antitrypsin fibrinogen, VIP (vasoactive intestinal peptide) and substance P were used, the trypsin-like enzyme obtained in Example 1 was reacted with each of them, and the digestion of each substrate was detected by SDS-polyacrylamide gel electrophoresis. As a result, only fibrinogen and VIP were specifically digested, and the other natural substrates were not digested.

TABLE 2

Influence of protease inhibitors on trypsin-like enzyme

| | | Inhibition (%) | | |
|---|---|---|---|---|
| Inhibitor | Concentration (μM) | Trypsin-like protease (human) | Neutrophile elastase (human) | Tryptase (derived from rat mast cell) |
| DFP | 10 | 100 | 100 | 100 |
| PMSF | 1000 | 100 | 93.6 | — |
| Leupeptin | 10 | 82.5 | 0 | 100 |
| Antipain | 10 | 78.1 | 11.1 | 98.2 |
| Elastinol | 10 | 0 | 0 | 53.0 |
| Bestatin | 10 | 0 | 15.2 | 23.4 |

TABLE 2-continued

Influence of protease inhibitors on trypsin-like enzyme

| Inhibitor | Concent- ration (μM) | Inhibition (%) | | |
|---|---|---|---|---|
| | | Trypsin- like protease (human) | Neutrophile elastase (human) | Tryptase (derived from rat mast cell) |
| Amastatin | 10 | 0 | 67.6 | 6.6 |
| α–1–antitrypsin | 10 | 23.5 | 100 | 66.3 |

EXAMPLE 6

Influence of trypsin-like enzyme on coagulation of fibrinogen

Figure 3:
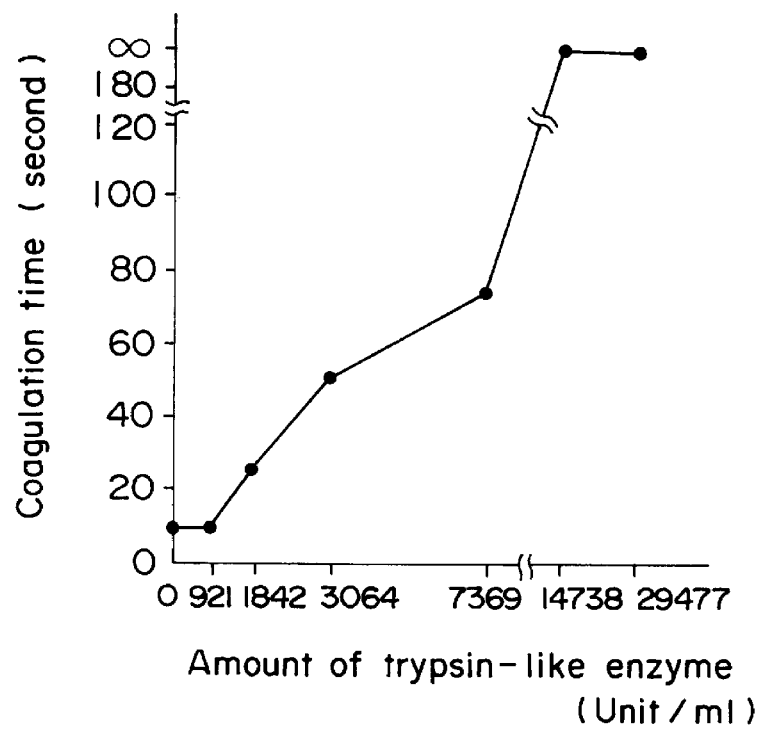
FIG. 3 is a graph showing the influence of the trypsin-like enzyme obtained in Example 1 on the thrombin-induced coagulation time of fibrinogen.

Fibrinogen was dissolved in 0.01M Tris-HCl buffer (pH 7.4), 0.01M $CaCl_2$ 0.15M NaCl so that its concentration could be 2 mg/ml, the trypsin-like enzyme obtained in Example 1 was added with its activity unit changed, the mixture was heated to 37° C., 0.1 ml of this reaction solution was mixed with 0.1 ml of a thrombin solution (2.5 units/ml), and coagulation time was measured on the mixture. The results are shown in FIG. 3. In proportion as the added activity unit of the trypsin-like enzyme increases, coagulation time was prolonged.

EXAMPLE 7

N-terminus amino acid sequence of trypsin-like enzyme

The trypsin-like enzyme obtained in Example 1 was subjected to reverse-phase HPLC (Vydac2l4TP54), and the enzyme was eluted with an acetonitrile concentration of 50.4%. The eluate was concentrated by distilling out the solvent, and subjected as such to a protein sequencer (Applied Biosystems Model 477A) to analyze the N-terminus amino acid sequence.

As a result, the sequence of up to the 20th residue from the N-terminus of the trypsin-like enzyme was Ile-Leu-Gly-Gly-Thr-Glu-Ala-Glu-Gl -Gly-Ser-Trp-Pro-Trp-Gln-Val-Ser-Leu-Arg-Leu (SEQ ID NO:1)

EXAMPLE 8

Cloning of cDNA 59bp encoding the N-terminus amino acid sequence 20 residues of the trypsin-like enzyme isolated from cough phlegm A. Preparation of oligonucleotide mixtures TRY-0 and TRY-00

An oligonucleotide mixture capable of encoding the 1st to 7th amino acids, shown by Sequence No. 2 was designed based on the amino acid sequence determined in Example 7, taking the degeneracy of the corresponding codons into account, and named TRY-0. Further, the complementary strand of a sequence capable of encoding the 15th to 20th amino acids, namely an oligonucleotide mixture shown by Sequence No. 3 was designed, and named TRY-00. These were synthesized by Applied Biosystems Model 394 DNA/RNA Synthesizer, and purified using OPC (Oligonucleotide Purification Cartridge) columns.

B. PCR on human trachea cDNA

PCR was conducted with a reaction volume of 20 μl per 1 ng of human trachea QUICK-Clone cDNA (LOT#23022) produced by CLONTECH Co., using 0.1 μg each of the oligonucleotide mixtures TRY-0 and TRY-00 prepared in Example 8A as primers and ampliTaq DNA polymerase. The PCR was conducted by using DNA Thermal Cycler produced by Perkin-Elmer Cetus Instruments Co., repeating 35 times a reaction cycle of 94° C. 1 min, 57° C. 1 min and 30 sec and 72° C. 2 min, and finally conducting incubation at 72° C. for 7 minutes, and thereby a PCR reaction mixture was obtained.

C. Preparation of a 59 bp PCR-amplified product fragment

To 20 μl of the PCR reaction mixture obtained in Example 8B was added an equal volume of chloroform, and the mixture was vigorously stirred. The mixture was then centrifuged, and the aqueous phase as the upper layer was transferred to a new tube. To this solution were added NaOAc in such an amount that its final concentration became 0.3M, and 2.5 volumes of ethanol, and the mixture was mixed. The resultant solution was allowed to stand at −80° C. for 20 minutes and centrifuged, and DNAs were pelletized. The pellets were rinsed with 70% ethanol, dissolved in 10 μl of TE buffer (10 mM Tris-HCl pH 8.0 and 1 mM EDTA), subjected to 5.6% polyacrylamide gel (29:1, acrylamide : bis-acrylamide) electrophoresis, and electrophoresed until a 59 bp DNA fragment was separated from the other PCR products. The gel was first stained with a dilute solution of ethidium bromide, and then DNA bands were checked by observing this gel under ultraviolet rays.

A region containing the 59 bp fragment was cut off from the gel, put in a microcentrifugation tube, and made into pieces. 400 μl of an extraction buffer (500 mM $NH_4OAc$ : 0.1 % SDS : and 1 mM EDTA, pH 7.5) was put in the microcentrifugation tube containing these gel pieces, and the mixture was left alone at 37° C. overnight. The mixture was then centrifuged, the residue was pelletized, and the supernatant was transferred to a new tube. To this supernatant were added NaOAc in such an amount that its final concentration became 0.3M, and 2.5 volumes of ethanol, and the mixture was mixed. The resultant solution was allowed to stand at −80° C. for 20 minutes and centrifuged, and DNAs were pelletized. The pellets were rinsed with 70% ethanol, and the resultant purified fragment was dissolved in 10 μl of TE buffer.

D. Assembly of plasmid p59-14

The fragment obtained in Example 8C was ligated to the SmaI cleavage site of a plasmid vector pUC 18 at the blunt ends using SureClone Ligation Kit produced by Pharmacia Co. Then, a competent E. coli JM109 cell produced by Takara Co. was transformed with the resultant plasmid according to the method described in Maniatis et al., Molecular Cloning: A Laboratory Manual, Cold Spring Harbor Laboratory, 1982.

From the resultant transformant, a p59-14 clone was selected based on its ampicillin resistance phenotype, and the length of a product obtained by PCR, for amplifying the insertion part, using a primer having a sequence near the SmaI cleavage site of the plasmid vector pUC 18, and by preparing a plasmid from a positive clone, p59-14 was obtained. The preparation of the plasmid was conducted by culturing an E. coli carrying the plasmid at 37° C. overnight on about 25 $cm^2$ of L broth agar medium (1% peptone, 1% NaCl, 0.5% yeast extract and 1.5% agar) containing 50 μg/ml of ampicillin, and then using QIAGEN Plasmid Kit produced by QIAGEN Co.

E. DNA sequencing of plasmid p59-14 insertion part

The plasmid p59-14 insertion part obtained in Example 8D was sequenced according to the dideoxy method (Sanger et al ., Proc. Natl. Acad. Sci . USA, 74: pages 5463–5467, 1977). The DNA sequence of the plasmid p59-14 insertion part is shown in Sequence No. 4. This p59-14 insertion part encodes the N-terminus amino acid sequence 19 residues of the trypsin-like enzyme isolated from the cough phlegm, and was identified as part of the desired trypsin-like enzyme cDNA.

EXAMPLE 9

Cloning of cDNA region encoding trypsin-like enzyme isolated from cough phlegm

A. Preparation of oligonucleotides TRY-1, TRY-8, TRY-10 and TRY-11

An oligonucleotide shown by Sequence No. 5, corresponding to from the first A to the 23rd A of Sequence No. 4, was designed based on the sequence of part of a cDNA encoding the trypsin-like enzyme, determined in Example 8, and named TRY-1. Similarly, an oligonucleotide shown by Sequence No. 6, corresponding to from the 16th G to the 40th T of Sequence No. 4, was designed, and named TRY-8. Further, an oligonucleotide shown by Sequence No. 7, capable of annealing to the 3'-terminus of poly(A)+RNA was designed, and named TRY-10. Further, an oligonucleotide shown by Sequence No. 8, which is identical to the 5'-terminus side 19 residues of TRY-10, was designed, and named TRY-11.

These were synthesized by Applied Biosystems Model 394 DNA/RNA Synthesizer, and purified using OPC columns produced by the same company.

B. Preparation of single-strand cDNA corresponding to human trachea poly(A)+RNA using TRY-10

10 ng of human trachea poly(A)+RNA (LOT#26105) obtained from CLONTECH was made to be an aqueous solution of 9 pl. This solution was subjected to incubation at 65° C. for 3 minutes, and the vessel containing the solution was immediately put in an ice bath for 5 minutes. A single-strand cDNA was prepared in a reaction volume of 20 μl using the above solution and, as a primer, 10 ng of an oligonucleotide TRY-10 prepared in Example 9A, and using a cDNA Synthesis Kit produced by Boehringer.Mannheim Co.

C. Amplification by PCR of cDNA region encoding trypsin-like enzyme isolated from cough phlegm PCR was conducted with a reaction volume of 20 μl per a ¹⁄₁₀ amount of the single-strand cDNA obtained in Example 9B using human trachea poly(A)+RNA as a template, using 0.1 μg each of the oligonucleotides TRY-1 and TRY-11 prepared in Example 9A as primers and ampliTaq DNA polymerase. The PCR was conducted by repeating 35 times a reaction cycle of 94° C. 1 min, 57° C. 1 min and 30 sec and 72° C. 2 min, and finally conducting incubation at 72° C. for 7 minutes, and thereby the first PCR reaction mixture was obtained.

Further, PCR was conducted with a reaction volume of 20 μl per a ¹⁄₄₀ amount of the PCR reaction mixture, using 0.1 μg each of the oligonucleotides TRY-8 and TRY-10 prepared in Example 9A as primers and ampliTaq DNA polymerase. The PCR was conducted by repeating 35 times a reaction cycle of 94° C. 1 min, 57° C. 1 min and 30 sec and 72° C. 2 min, and finally conducting incubation at 72° C. for 7 minutes, and thereby the second PCR reaction mixture was obtained. It was confirmed by 5.6% polyacrylamide gel electrophoresis that in this second PCR reaction mixture, about 900 bp of DNA was selectively amplified.

D. Preparation of the second PCR amplified product fragment

To 20 μl of the second PCR reaction mixture obtained in Example 9C was added an equal volume of chloroform, and the mixture was vigorously stirred. The mixture was then centrifuged, and the aqueous phase as the upper layer was transferred to a new tube. To this solution were added NaOAc in such an amount that its final concentration became 0.3M, and 2.5 volumes of ethanol, and the mixture was mixed. The resultant solution was allowed to stand at −80° C. for 20 minutes and centrifuged, and DNAs were pelletized. The pellets were rinsed with 70% ethanol, dissolved in 10 μl of TE buffer, subjected to 2% low melting point agarose gel electrophoresis, and electrophoresed until an about 900 bp DNA fragment was separated from the other PCR products. The gel was first stained with a dilute solution of ethidium bromide, and then DNA bands were checked by observing this gel under ultraviolet rays.

A region containing the about 900 bp DNA fragment was cut off from the gel, put in a microcetrifugation tube. TE buffer was put in the microcetrifugation tube containing the gel pieces so that the whole volume could be 400 μl, and the mixture was subjected to incubation until the agarose gel was dissolved. To this solution was added an equal volume of phenol-saturated TE buffer previously adjusted to a temperature 65° C., and the mixture was vigorously stirred and centrifuged, and the aqueous phase as the upper layer was transferred to a new tube. The operations were repeated again. Then, to the resultant solution was added an equal volume of chloroform, and the mixture was vigorously stirred. The mixture was then centrifuged, and the aqueous phase as the upper layer was transferred to a new tube. To this solution were added NaOAc in such an amount that its final concentration became 0.3M, and 2.5 volumes of ethanol, and the mixture was mixed. The resultant solution was allowed to stand at −80° C. for 20 minutes and centrifuged, and DNAs were pelletized. The pellets were rinsed with 70% ethanol, and the resultant purified fragment was dissolved in 10 pl of TE buffer.

E. Assembly of plasmid p19-33

The fragment obtained in Example 9D was ligated to the SmaI cleavage site of a plasmid vector pUC 18 at the blunt ends using SureClone Ligation Kit produced by Pharmacia Co. Then, a competent *E. coli* JM109 cell produced by Takara Co. was transformed with the resultant plasmid. From the resultant transformant, a p19-33 clone was selected based on its ampicillin resistance phenotype, and the length of a product obtained by PCR, for amplifying the insertion part, using a primer having a sequence near the SmaI cleavage site of the plasmid vector pUC 18, and by preparing a plasmid from a positive clone, p19-33 was obtained.

F. DNA sequencing of plasmid pl9-33 insertion part

The insertion part of the plasmid p19-33 obtained in Example 9E was sequenced according to the dideoxy method (Sanger et al., Proc. Natl. Acad. Sci. USA, 74: pages 5463–5467, 1977). The DNA sequence of the plasmid p19-33 insertion part is shown in Sequence No. 9. This p19-33 insertion part encodes part of the N-terminus amino acid sequence 20 residues of the trypsin-like enzyme isolated from the cough phlegm, and was identified as part of the desired trypsin-like enzyme cDNA.

EXAMPLE 10

Cloning of the upstream region of trypsin-like enzyme cDNA

A. Preparation of oligonucleotides TRY-25 and TRY-26

An oligonucleotide shown by Sequence No. 10, which is complementary to the sequence of from the 127th A to the 151st T of Sequence No. 9, was designed, and named TRY-25. Similarly, an oligonucleotide shown by Sequence No. 11, which is complementary to the sequence of from the 83rd A to the 107th A of Sequence No. 9 was designed, and named TRY-26.

These were synthesized by Applied Biosystems Model 394 DNA/RNA Synthesizer, and purified using OPC columns produced by the same company.

B. Preparation of anchor ligation single-strand cDNA corresponding to human trachea poly(A)+RNA using TRY-25

Reverse transcription reaction was conducted on 2 µg of human trachea poly(A)+RNA (LOT# 29099) obtained from CLONTECH, using 5'-AmpliFINDER RACE Kit produced by CLONTECH Co., and using 83 ng of the oligonucleotide TRY-25 prepared in Example 10A as a primer, and thereby a single-strand cDNA was synthesized. Then, the RNA in the reaction mixture was alkali hydrolyzed, neutralization was conducted, and the single-strand cDNA was purified using glass powder contained in the kit. AmpliFINDER anchor shown by Sequence No. 12 in the kit was ligated to the 3'-terminus of this single-strand cDNA using a T4 RNA ligase.

C. Amplification by PCR of the upstream region of trypsin-like enzyme cDNA

PCR was conducted with a reaction volume of 50 µl per a 1/100 amount of the anchor ligation single-strand cDNA corresponding to human trachea poly(A)+RNA obtained in Example 10B, using the oligonucleotide TRY-26, and AmpliFINDER anchor primer contained in 5'-AmpliFINDER RACE Kit produced by CLONTECH Co., shown in Sequence No. 13, as primers, in each final concentration of 0.2 µM, and using ampliTaq DNA polymerase. The PCR was conducted by repeating 35 times a reaction cycle of 94° C. 45 sec, 60° C. 45 sec and 72° C. 2 min, and finally conducting incubation at 72° C. for 7 minutes, and thereby a PCR reaction mixture was obtained. It was confirmed by 5.6 % polyacrylamide gel electrophoresis that in this PCR reaction mixture, about 790 bp of DNA was selectively amplified.

D. Preparation of the PCR amplified product fragment

To 40 µl of the PCR reaction mixture obtained in Example 10C was added an equal volume of chloroform, and the mixture was vigorously stirred. The mixture was then centrifuged, and the aqueous phase as the upper layer was transferred to a new tube. To this solution were added NaOAc in such an amount that its final concentration became 0.3M, and 2.5 volumes of ethanol, and the mixture was mixed. The resultant solution was allowed to stand at −80° C. for 20 minutes and centrifuged, and DNAs were pelletized. The pellets were rinsed with 70% ethanol, dissolved in 10 µl of TE buffer, subjected to 5.6% polyacrylamide gel (29:1, acrylamide:bis-acrylamide) electrophoresis, and electrophoresed until an about 790 bp DNA fragment was separated from the other PCR products. The gel was first stained with a dilute solution of ethidium bromide, and then DNA bands were checked by observing this gel under ultraviolet rays.

A region containing the about 790 bp DNA fragment was cut off from the gel, put in a microcetrifugation tube, and made into small pieces. 400 µl of an extraction buffer (500 mM NH$_4$OAc:0.1% SDS:and 1 mM EDTA, pH 7.5) was put in the microcetrifugation tube containing these gel pieces so that the whole volume could be 400 µl, and the mixture was left alone at 37° C. overnight. Then, the mixture was centrifuged, the residue was pelletized, and the supernatant was transferred to a new tube. To this supernatant were added NaOAc in such an amount that its final concentration became 0.3M, and 2.5 volumes of ethanol, and the mixture was mixed. The resultant solution was allowed to stand at −80° C. for 20 minutes and centrifuged, and DNAs were pelletized. The pellets were rinsed with 70% ethanol, and the resultant purified fragment was dissolved in 10 µl of TE buffer.

E. Assembly of plasmid p5-119

The fragment obtained in Example 10D was ligated to the SmaI cleavage site of a plasmid vector pUC 18 at the blunt ends using SureClone Ligation Kit produced by Pharmacia Co. Then, a competent *E. coli* JM109 cell produced by Takara Co. was transformed with the resultant plasmid. From the resultant transformant, a p5-119 clone was selected based on its ampicillin resistance phenotype, and the length of a product, for amplifying the insertion part, obtained by PCR using a primer having a sequence near the SmaI cleavage site of the plasmid vector pUC 18, and by preparing a plasmid from a positive clone, p5-119 was obtained.

F. DNA sequencing of plasmid p5-119 insertion part

The insertion part of the plasmid p5-119 obtained in Example 10E was sequenced according to the dideoxy method (Sanger et al., Proc. Natl. Acad. Sci. USA, 74: pages 5463–5467, 1977). The DNA sequence of the plasmid p5-119 insertion part is shown in Sequence No. 14. This insertion part of 789 bp contains a region encoding the N-terminus amino acid sequence 20 residues of the trypsin-like enzyme isolated from the cough phlegm, and was identified as part of the desired trypsin-like enzyme cDNA.

EXAMPLE 11

Determination of trypsin-like enzyme gene cDNA sequence

The overlap parts of 107 bp between the sequences determined in Examples 9 and 10 were identified, respectively, and thereby their identity was confirmed. It was confirmed from the sequence analysis that these ovelaping sequences contained a region encoding the amino acids of the N-terminus 20 residues of the trypsin-like enzyme isolated from the cough phlegm. From the foregoing, the sequences were ligated, and the desired trypsin-like enzyme gene cDNA sequence was determined. These DNA and amino acid sequence are shown in Sequence No. 15

EXAMPLE 12

Assembly of plasmid pPHAT1

Figure 4:
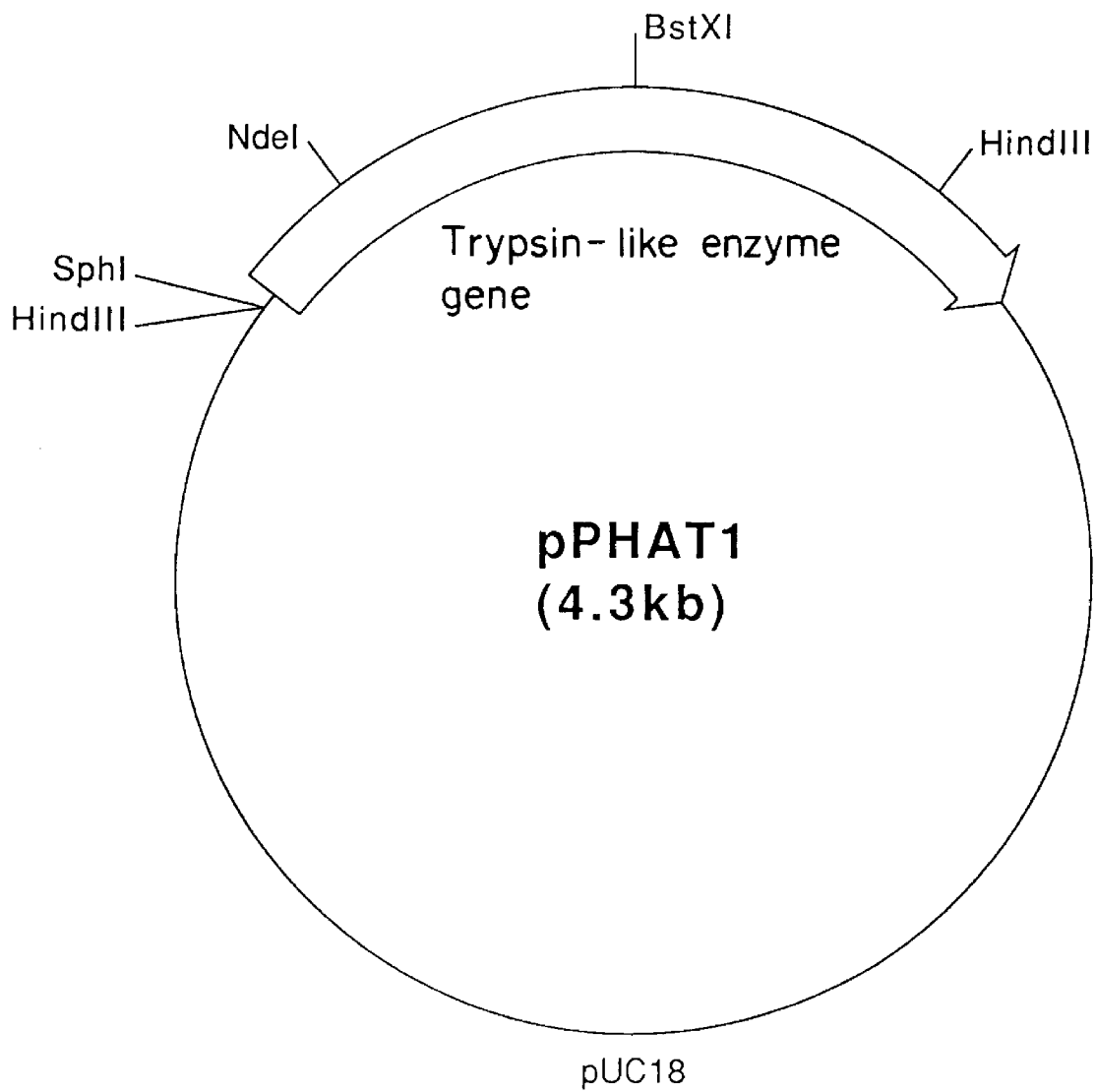
FIG. 4 is a restriction enzyme map showing the plasmid pPHAT1 having the trypsin-like enzyme gene obtained in Example 12.

The plasmid p19-33 obtained in Example 9 and the plasmid p5-119 obtained in Example 10 were, separately, cleaved with SphI and BstXI. A SphI-BstXI fragment of about 3.6 kb derived from p19-33 and a SphI-BstXI fragment of about 0.7 kb derived from p5-119 were separated and isolated by agarose electrophoresis. Ligation reaction was conducted on these two SphI-BstXI fragments, and an *Escherichia coli* JM 109 strain was transformed with the ligation product. By preparing plasmids from several transformants, a plasmid ppHAT1 was obtained (FIG. 4).

EXAMPLE 13

Figure 5:
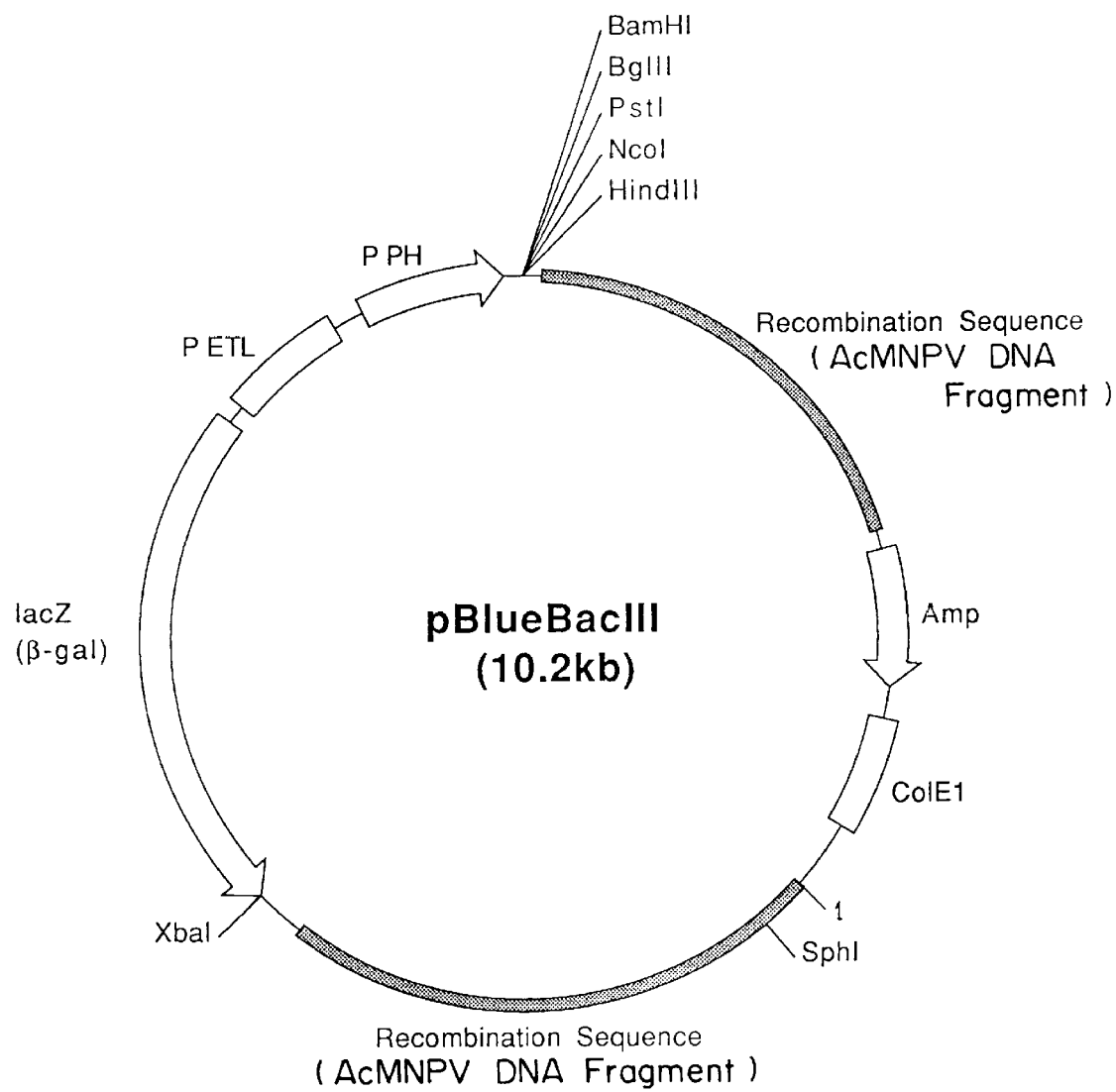
FIG. 5 is a restriction enzyme map showing a starting vector pBlueBac III for creating a recombinant vector.

Assembly of recombinant vector into which cDNA encoding trypsin-like enzyme was inserted pBlueBacIII (Invitrogen) was used as an expression vector. The sequence of this vector pBlueBacIII is shown in Sequence No. 16, and its restriction sites and function map are shown in FIG. 5. As shown in FIG. 5, pBlueBacIII has the AcMNPV gene. This AcMNPV gene (Autographa californica multiple nuclear polyhedrosis virus gene) is disclosed in the following literature.

R. D. Posse et al., Virology, 185 (1991), pp.229–241.

Figure 6:
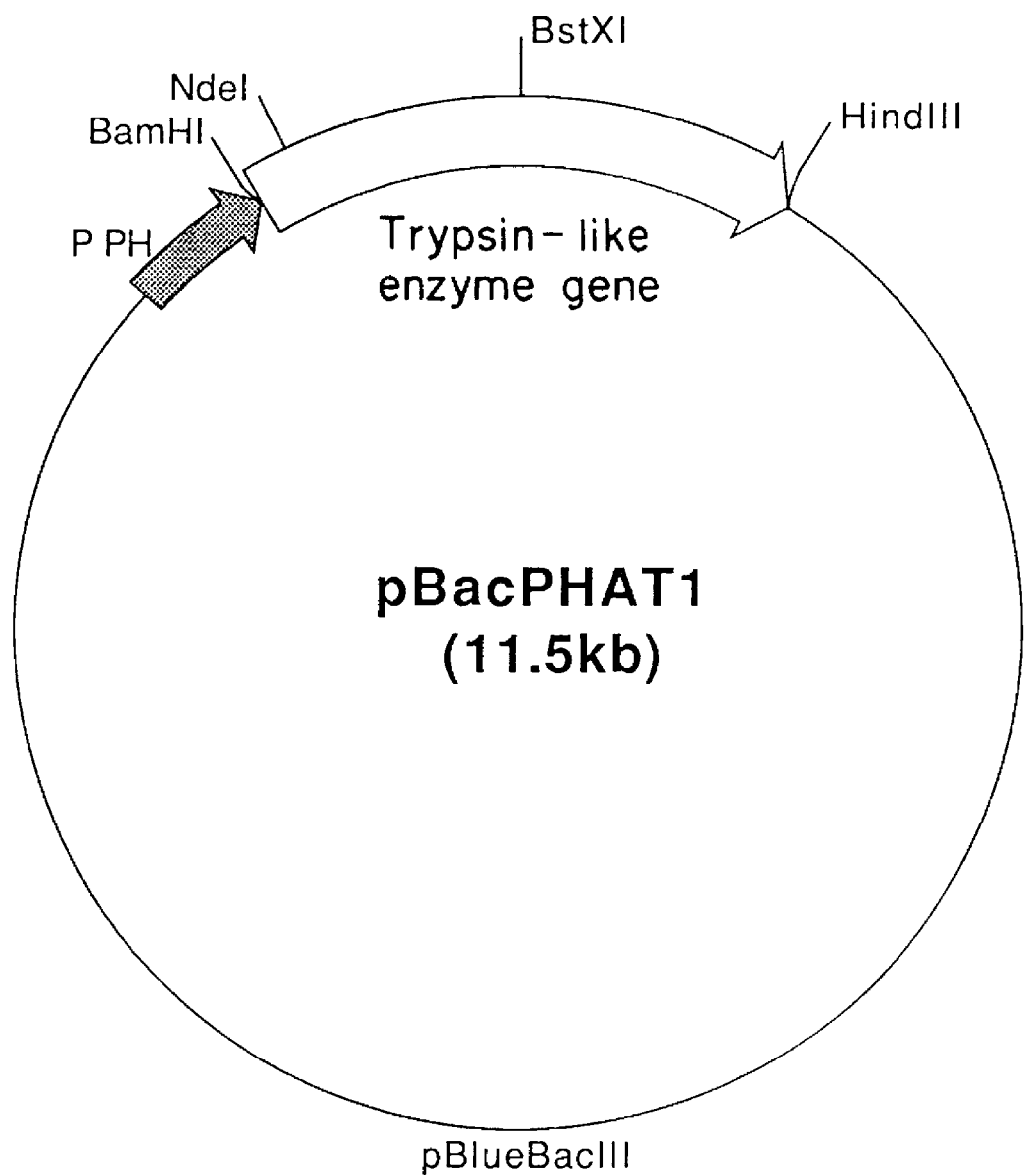
FIG. 6 is a restriction enzyme map showing the vector for homologous recombination pBacPHAT1 obtained in Example 6.

This pBlueBacIII was cleaved with BamHI and HindIII, and to this were ligated a BamHI-NdeI fragment obtained by annealing the two single-strand DNAs shown in Sequence Nos. 17 and 18, and a NdeI-Hind III fragment separated and isolated by cleaving pPHAT1 with NdeI and HindIII and subjecting the cleavage products to agarose electrophoresis. An Escherichia coli HB101 strain was transformed using the ligation product. By preparing plasmids from the resultant several tramsformants, a vector pBacPHAT1 for homologous recombination was obtained (FIG. 6).

EXAMPLE 14

Preparation of recombinant baculovirus

AcMNPV was cleaved at one position with Eco81I to make it linear, the obtained matter was mixed with 1 µg of pBacPHAT1, and the volume of the mixture was made to be 8 µl with sterilized water. To this was added an equal volume of lipofectin (GIBCO Co.) diluted two-fold, and the mixture was allowed to stand at room temperature for 15 minutes, and then added to 1.5 ml of a serum-free medium EX-CELL 400 (JRH Bio Science) containing $1 \times 10^6$ of an insect cell SF-9 in a dish. After the cell was cultured for 3 days, the medium was recovered and appropriately diluted, e.g. 10-fold, 100-fold or the like, and SF-9 monolayer cultured was infected with the dilution to form plaques. After 3 days culture, X-gal was added to the medium, and on the next day, recombinant baculoviruses stained blue and colorless, transparent non-recombinant baculoviruses are separated. The blue-stained plaques were sucked up by a Pasteur pipet and suspended in a medium, and thereafter, this virus solution was appropriately diluted again, an insect cell was infected with the dilution, and the cell was cultured. In the manner as stated above, isolation was repeated until all plaques appearing were stained blue. The thus obtained recombinant baculovirus was named #1B3.

EXAMPLE 15

Production of trypsin-like enzyme by recombinant baculovirus

SF-9 cells were grown in a monolayer until a density of $5 \times 10^6$ cells/ml, the medium was removed, a serum-free medium containing 2 to 5 pfu of #1B3 per cell was added to infect the cells, and the cells were cultured for 4 days to express a trypsin-like enzyme. Confirmation of the expressed protein was conducted by Western blot technique (Anal. Biochem., 112, 195–203, 1981) using SDS-PAGE and an anti-trypsin-like enzyme peptide antibody.

Figure 7:
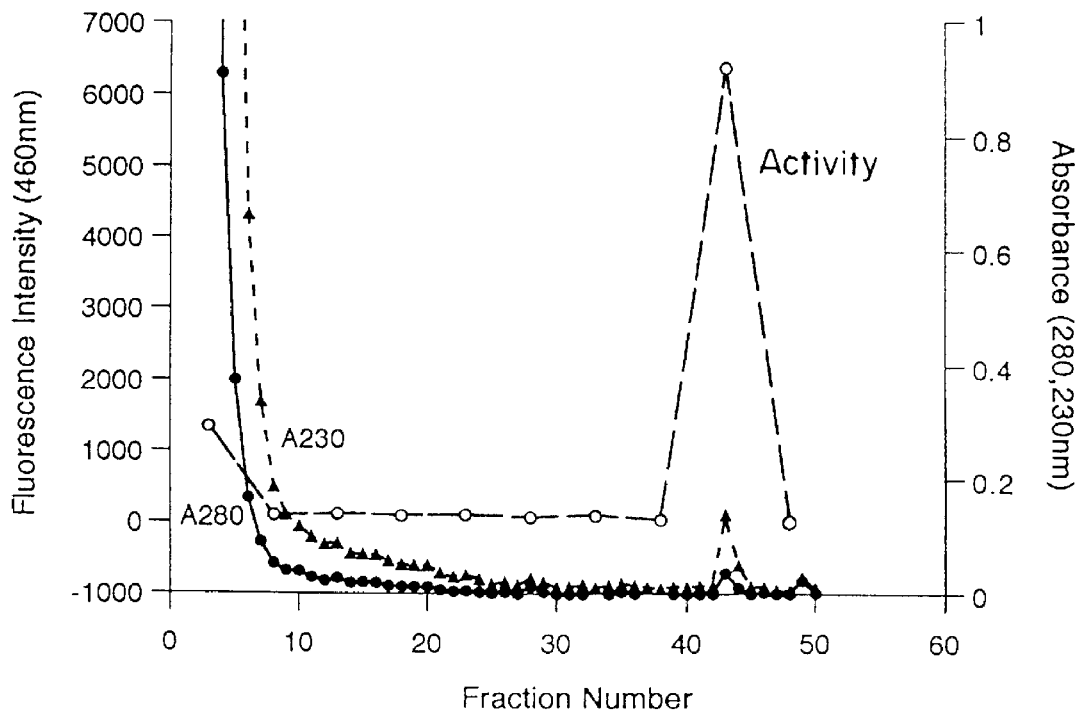
FIG. 7 is a drawing showing the relation between the affinity column elution fractions obtained in Example 15 and their activities.

The supernatant and the cells were separated by centrifugation (about 500×g), the supernatant was subjected to ultrafiltration (Fujifilter Filtron Miniset; cut-off molecular weight 300 kDa) to remove the virus, and the resultant solution was dialyzed against or diluted with 50 mM Tris hydrochloric acid—500 mM sodium chloride buffer (pH 8.0) overnight. The cells were suspended in 50 mM Tris hydrochloric acid—500 mM sodium chloride buffer (pH 8.0), Triton X-100 was added so that its final concentration could be 1%, and the mixture was left alone at 0° C. for 60 minutes to lyse the cells. The cell debris was centrifuged, and the supernatant was dialyzed against or diluted with 50 mM Tris hydrochloric acid—500 mM sodium chloride buffer (pH 8.0) overnight. The solution was loaded on a benzamidine affinity column (Pharmacia) equilibrated with 50 mM Tris hydrochloric acid—500 mM sodium chloride buffer (pH 8.0), and washed with the same buffer, and elution was conducted with 10 mM hydrochloric acid—500 mM sodium chloride solution (pH 2.0). Trypsin-like enzyme activity was assayed and detected on each fraction according to the method shown in Example 2 (FIG. 7), the main peaks were collected, SDS-PAGE was conducted to detect a protein having a molecular weight of about 28 kDa, and it was confirmed, by the western blot technique using an anti-trypsin-like enzyme peptide antibody, that this 28 kDa protein was a trypsin-like enzyme.

Figure 8:
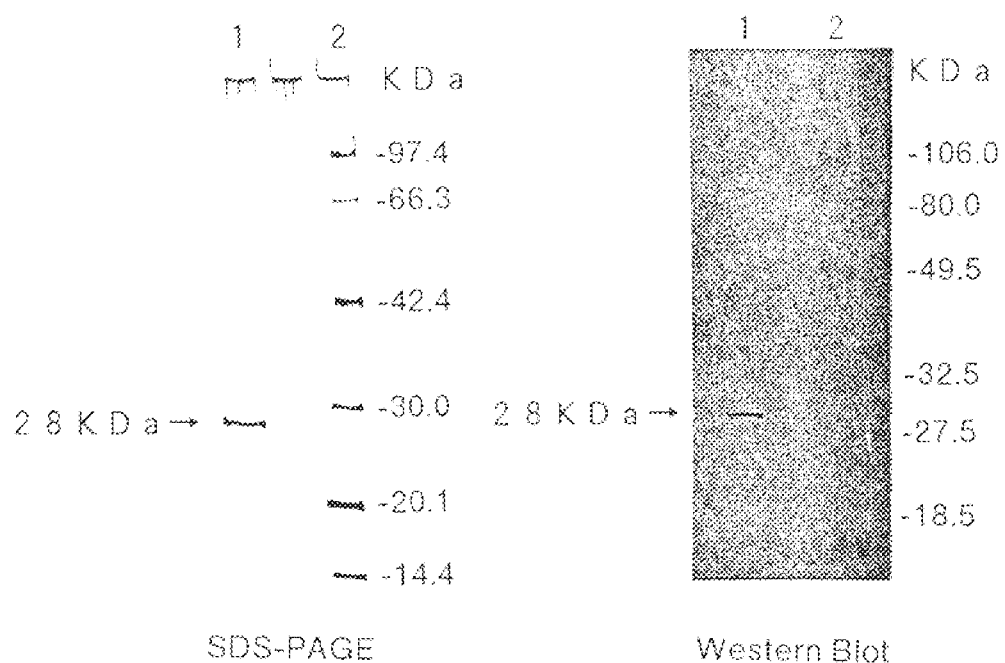
FIG. 8 is the SDS-PAGE and Western Blot of the purified trypsine-like enzyme obtained in Example 15.

The thus obtained purified trypsin-like enzyme exhibits one band in SDS-PAGE. The results of the SDS-PAGE and western blotting of the trypsin-like enzyme isolated from the infected cells are shown in FIG. 8. The N-terminus amino acid sequence of this purified sample was determined by a protein sequencer (Applied Biosystems Model 477A), and as a result it coincided with that of a natural trypsin-like enzyme.

Reference example 1: Preparation of anti-trypsin-like enzyme peptide polyclonal antibody A peptide of 20 residues wherein cysteine was disposed at the N-terminus of the sequence of from 1st residue to 19th residue of the mature trypsin-like enzyme was chemically synthesized by a peptide synthesizer (Applied Biosystems Model 431A). This synthetic peptide was dissolved in 10 mM phosphate buffer (pH 7.5) (10 mg/ml), and incubated at 25° C. for 2 hours with 10 mg of maleimide-activated hemocyanin (Boehringer Mannheim Biochemica), and the reaction solution was dialyzed against 10 mM phosphate buffer (pH 7.5). The peptide bound to hemocyanin was subcutaneously administered (0.5 mg/once) to a rabbit. Administration was repeated 6 times every two weeks. The rabbit was exsanguinated, and serum was prepared from the blood, and purified by a protein A-Sepharose-4B (Pharmacia) column to give an anti-trypsin-like enzyme peptide polyclonal antibody.

What is claimed is:

1. A nucleic acid sequence encoding a trypsin-like enzyme having the following amino acid sequence:

Ile Leu Gly Gly Thr Glu Ala Glu Glu Gly Ser Trp Pro
1                 5                     10
Trp Gln Val Ser Leu Arg Leu Asn Asn Ala His His Cys
        15                  20                      25
Gly Gly Ser Leu Ile Asn Asn Met Trp Ile Leu Thr Ala
                30                  35
Ala His Cys Phe Arg Ser Asn Ser Asn Pro Arg Asp Trp
40                      45                      50
Ile Ala Thr Ser Gly Ile Ser Thr Thr Phe Pro Lys Leu
            55                  60                      65
Arg Met Arg Val Arg Asn Ile Leu His Asn Asn Tyr Lys
                    70                      75
Ser Ala Thr His Glu Asn Asp Ile Ala Leu Val Arg Leu
80                      85                      90
Glu Asn Ser Val Thr Phe Thr Lys Asp Ile His Ser Val
            95                      100                 105
Cys Leu Pro Ala Ala Thr Gln Asn Ile Pro Pro Gly Ser
                    110                     115

Thr Ala Tyr Val Thr Gly Trp Gly Ala Gln Glu Tyr Ala
        120                     125                     130
Gly His Thr Val Pro Glu Leu Arg Gln Gly Gln Val Arg
                    135                     140
Ile Ile Ser Asn Asp Val Cys Asn Ala Pro His Ser Tyr
145                     150                     155
Asn Gly Ala Ile Leu Ser Gly Met Leu Cys Ala Gly Val
            160                     165                 170
Pro Gln Gly Gly Val Asp Ala Cys Gln Gly Asp Ser Gly
                        175                     180
Gly Pro Leu Val Gln Glu Asp Ser Arg Arg Leu Trp Phe
        185                     190                     195
Ile Val Gly Ile Val Ser Trp Gly Asp Gln Cys Gly Leu
            200                     205
Pro Asp Lys Pro Gly Val Tyr Thr Arg Val Thr Ala Tyr
210                     215                     220
Leu Asp Trp Ile Arg Gln Gln Thr Gly Ile (SEQ ID NO. 19)
        225                     230

2. The nucleic acid sequence according to claim 1 has the following sequence:

ANC CNN GGA GGC ACN GAG GCN GAG GAG GGA AGC NGG CCG NGG CAA GNC
AGN CNG CGG CNC AAN AAN GCC CAC CAC NGN GGA GGC AGC CNG ANC AAN
AAC ANG NGG ANC CNG ACA GCA GCN CAC NGC NNC AGA AGC AAC NCN AAN
CCN CGN GAC NGG ANN GCC ACG NCN GGN ANN NCC ACA ACA NNN CCN AAA
CNA AGA ANG AGA GNA AGA AAN ANN NNA ANN CAN AAC AAN NAN AAA NCN
GCA ACN CAN GAA AAN GAC ANN GCA CNN GNG AGA CNN GAG AAC AGN GNC
ACC NNN ACC AAA GAN ANC CAN AGN GNG NGN CNC CCA GCN GCN ACC CAG
AAN ANN CCA CCN GGC NCN ACN GCN NAN GNA ACA GGA NGG GGC GCN CAA
GAA NAN GCN GGC CAC ACA GNN CCA GAG CNA AGG CAA GGA CAG GNC AGA
ANA ANA AGN AAN GAN GNA NGN AAN GCA CCA CAN AGN NAN AAN GGA GCC
ANC NNG NCN GGA ANG CNG NGN GCN GGA GNA CCN CAA GGN GGA GNG GAC
GCA NGN CAG GGN GAC NCN GGN GGC CCA CNA GNA CAA GAA GAC NCA CGG
CGG CNN NGG NNN ANN GNG GGG ANA GNA AGC NGG GGA GAN CAG NGN GGC

-continued
```
CNG CCG GAN AAG CCA GGA GNG NAN ACN CGA GNG ACA GCC NAC CNN GAC

NGG ANN AGG CAA CAA ACN GGG ANC
``` wherein N represents T or U (SEQ ID No. 23).

3. The nucleic acid sequence of claim 2, having the DNA sequence depicted in SEQ ID NO. 24.

4. A recombinant expression vector comprising the nucleic acid of claim 1 or claim 3.

5. A host cell transformed with the expression vector of claim 4.

6. A process for producing a trypsin-like enzyme having the amino acid sequence according to SEQ ID NO. 19, comprising culturing a transformed host according to claim 5, and recovering the trypsin-like enzyme from said culture.

7. A purified trypsin-like enzyme having the amino acid sequence set forth in SEQ ID NO. 19.

8. A purified prepro-trypsin-like enzyme having the amino acid sequence set forth in SEQ ID NO. 25.

9. A purified trypsin-like enzyme obtained from phlegm, said trypsin-like enzyme having a molecular weight of 28 kD on SDS-PAGE and having the following activities:
 a) digests synthetic substrates for trypsin or for thrombin, said substrates selected from the group consisting of Boc-Phe-Ser-Arg-methylcoumarinamide (MCA), Boc-Gln-Ala-Arg-MCA, and Boc-Val-Pro-Arg-MCA,
 b) does not digest synthetic substrates for chymotrypsin, elastase, collagenase, or for leucine aminopeptidase,
 c) is inactivated at pH 6.0,
 d) is inhibited by diisopropyl fluorophosphate (DFP), phenylmethylsulfonyl fluoride (PMSF), leupeptin, and antipain, and
 e) inactivates influenza viruses.

* * * * *